US012653866B2

(12) United States Patent
Akers et al.

(10) Patent No.: US 12,653,866 B2
(45) **Date of Patent: *Jun. 16, 2026**

(54) URI AGONIST/VASODILATOR

(71) Applicant: Eli Lilly and Company, Indianapolis, IN (US)

(72) Inventors: Michael Patrick Akers, Indianapolis, IN (US); Chi A. Nguyen, Fishers, IN (US); Chad D. Paavola, Carmel, IN (US); Virender Kumar Sarin, Carmel, IN (US); Nanette Elizabeth Schulte, Indianapolis, IN (US); Ranajoy Majumdar, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/540,193

(22) Filed: Dec. 14, 2023

(65) Prior Publication Data

US 2024/0238382 A1 Jul. 18, 2024

Related U.S. Application Data

(63) Continuation of application No. 17/478,747, filed on Sep. 17, 2021, now Pat. No. 11,872,266, which is a continuation of application No. 15/978,329, filed on May 14, 2018, now Pat. No. 11,123,406, which is a continuation of application No. 14/963,279, filed on Dec. 9, 2015, now Pat. No. 9,993,555.

(60) Provisional application No. 62/092,407, filed on Dec. 16, 2014.

(51) Int. Cl.

| | |
|---|---|
| ***A61K 38/28*** | (2006.01) |
| ***A61K 9/00*** | (2006.01) |
| ***A61K 47/02*** | (2006.01) |
| ***A61K 47/10*** | (2017.01) |
| ***A61K 47/12*** | (2006.01) |
| ***A61P 3/10*** | (2006.01) |

(52) U.S. Cl.

CPC ............ *A61K 38/28* (2013.01); *A61K 9/0019* (2013.01); *A61K 47/02* (2013.01); *A61K 47/10* (2013.01); *A61K 47/12* (2013.01); *A61P 3/10* (2018.01)

(58) Field of Classification Search

None

See application file for complete search history.

(56) References Cited

U.S. PATENT DOCUMENTS

| | | | |
|---|---|---|---|
| 3,584,121 A | 6/1971 | Krayenbuhl et al. | |
| 4,476,118 A | 10/1984 | Brange et al. | |
| 4,885,164 A | 12/1989 | Thurow | |
| 5,045,454 A | 9/1991 | Bertheussen | |
| 5,164,366 A | 11/1992 | Balschmidt et al. | |
| 5,474,978 A | 12/1995 | Bakaysa et al. | |
| 5,716,927 A | 2/1998 | Balschmidt et al. | |
| 5,866,538 A | 2/1999 | Norup et al. | |
| 7,279,457 B2 | 10/2007 | Pohl et al. | |
| 7,696,162 B2 | 4/2010 | Boderke | |
| 7,713,930 B2 | 5/2010 | Brunner-Schwarz et al. | |
| 8,084,420 B2 | 12/2011 | Steiner et al. | |
| 9,901,623 B2 * | 2/2018 | Akers | A61K 47/10 |
| 9,993,555 B2 * | 6/2018 | Akers | A61P 3/10 |
| 11,123,406 B2 * | 9/2021 | Akers | A61K 47/02 |
| 2007/0086952 A1 | 4/2007 | Steiner et al. | |
| 2007/0206081 A1 | 9/2007 | Masada et al. | |
| 2007/0235365 A1 | 10/2007 | Pohl et al. | |
| 2008/0090753 A1 | 4/2008 | Pohl et al. | |
| 2008/0194461 A1 | 8/2008 | Maggio | |
| 2010/0167990 A1 | 7/2010 | Poulsen et al. | |
| 2010/0227795 A1 | 9/2010 | Steiner et al. | |
| 2010/0249020 A1 | 9/2010 | Soula et al. | |
| 2012/0094902 A1 | 4/2012 | Soula et al. | |
| 2012/0178675 A1 | 7/2012 | Pohl et al. | |
| 2013/0011378 A1 | 1/2013 | Yang et al. | |
| 2013/0022592 A1 | 1/2013 | Vaughn et al. | |
| 2013/0231281 A1 | 9/2013 | Soula et al. | |
| 2013/0302275 A1 | 11/2013 | Wei et al. | |
| 2014/0113856 A1 | 4/2014 | Pohl et al. | |
| 2014/0135682 A1 | 5/2014 | Frost et al. | |
| 2014/0357554 A1 | 12/2014 | Pohl et al. | |
| 2015/0065423 A1 | 3/2015 | Laulicht et al. | |
| 2015/0273022 A1 | 10/2015 | Wilson et al. | |
| 2020/0237877 A1 * | 7/2020 | Soula | A61K 47/02 |

FOREIGN PATENT DOCUMENTS

| | | |
|---|---|---|
| DK | 116527 B | 1/1970 |
| EP | 214826 | 3/1987 |
| EP | 280534 | 2/1988 |

(Continued)

OTHER PUBLICATIONS

Jens Brange, Stability of Insulin—Studies on the physical and chemical stability of insulin in pharmaceutical formulation, Kluwer Academic Publishers, 1994.
Document Aug. 16, 2021 opposition to European Patent No. EP3372238, Extract from NICE website insulin summary (https://bnt.nice.org/treatmentssummary/insulin-2.html).
Yoshinori Marunaka, World J. Diabetes, 2015, 6(1), pp. 125-135.
Steiner S. et al., A novel insulin formulation with a more repaid onset of action, Diabetologia (2008) 51:1602-1606.

(Continued)

*Primary Examiner* — Sergio Coffa
(74) *Attorney, Agent, or Firm* — Perry Woo

(57) ABSTRACT

The invention is a composition of human insulin or insulin analog that includes specific concentrations of citrate, chloride, in some cases including the addition of sodium chloride, zinc and, optionally, magnesium chloride and/or surfactant, and that has faster pharmacokinetic and/or pharmacodynamic action than commercial formulations of existing insulin analog products.

30 Claims, 1 Drawing Sheet

Specification includes a Sequence Listing.

(56) References Cited

FOREIGN PATENT DOCUMENTS

| | | | |
|---|---|---|---|
| JP | 2012519695 | T2 | 8/2012 |
| WO | 9733531 | | 9/1997 |
| WO | 9749386 | | 12/1997 |
| WO | 98/16205 | A1 | 4/1998 |
| WO | 9934821 | | 7/1999 |
| WO | 0043034 | | 7/2000 |
| WO | 0135943 | | 5/2001 |
| WO | 03000202 | | 1/2003 |
| WO | 2005089722 | A1 | 9/2005 |
| WO | 2007041481 | A1 | 4/2007 |
| WO | 2007121256 | A2 | 10/2007 |
| WO | 2008/013955 | A2 | 1/2008 |
| WO | 2008152106 | A1 | 12/2008 |
| WO | 2009034118 | A1 | 3/2009 |
| WO | 2009048959 | A1 | 4/2009 |
| WO | 2009134380 | A2 | 11/2009 |
| WO | 2010102020 | A1 | 9/2010 |
| WO | 2010/149772 | A1 | 12/2010 |
| WO | 12006283 | | 1/2012 |
| WO | 13158618 | | 10/2013 |
| WO | 13177565 | | 11/2013 |
| WO | 15106269 | | 7/2015 |
| WO | 15120457 | | 8/2015 |

OTHER PUBLICATIONS

Document Aug. 16, 2021 opposition to European Patent No. EP3372238, Letter dated Apr. 26, 2018.
Document Aug. 16, 2021 opposition to European Patent No. EP3372238, "Technical primer on ionization forms or citrate/citric acid".
Document Aug. 16, 2021 opposition to European Patent No. EP3372238, Letter dated Dec. 17, 2007.
Document Aug. 16, 2021 opposition to European Patent No. EP3372238, "Annex" to Letter dated Dec. 17, 2007.
Marunaka, Roles of Interstitial fluid pH in Diabetes Mellitus: Glycolysis and mitochondrial function, World J. Diabetes, 2015, 6(1), pp. 125-135.
Dr. Leo Polz, Applicant letter in response to official action in European Patent Application No. 05 728 268.3, dated Dec. 17, 2007.
Dr. Leo Polz, Experimental Results, Annex accompanying Applicant letter in response to official action in European Patent Application No. 05 728 268.3, dated Dec. 17, 2007.
Wright, Submission to the EPO in European Patent Application No. 18155633.3, dated Apr. 26, 2018.
Poon et al. (2010); Glargine and detemir: Safety and efficacy profiles of the long-acting basal insulin analogs; Drug, Healthcare and Patient Safety, 2: 213-223.
Radermecker and Scheen (2004) Continuous subcutaneous insulin infusion with short-acting insulin analogues or human regular insulin: efficacy, safety, quality of life, and cost-effectiveness; Diabetes Metab. Res. Rev. 20:178-188.
FDA label to Lantus (2007).
"Handbook of Insulin Therapies"; LANTUS; (Eds. Crasto W, Jarvis J, Davies MJ, Adis, 2016).
Table and graph showing pharmacokinetic characteristics of different insulin analogues, cited on Dec. 13, 2022 in Opposition to European Patent Application No. 18155633.3.
Screenshot of website "Diabetes Education Online" submitted on Dec. 13, 2022 in Opposition to European Patent Application No. 18155633.3.
European public assessment report (EPAR) related to APIDRA (insulin glulisine) submitted on Dec. 30, 2022 in Opposition to European Patent Application No. 18155633.3.
Becker RHA and Frick AD; Clinical Pharmacokinetics and Pharmacodynamics of Insulin Glulisine; Olin Phamacokinet 2008:47(1): 7-20.
Entry "Phosphatpuffer" in "apothekenwiki" (Oct. 21, 2015).
Bolli, G. B., & Owens, D. R. (2000). Insulin glargine. The Lancet, 356(9228), 443-445.
Extract from Novo Nordisk website; Our Medicines; submitted on Dec. 30, 2022 in Opposition to European Patent Application No. 18155633.3.
Pohl, Roderike, et al., Ultra-Rapid Absorption of Recombinant Human Insulin Induced by Zinc Chelation and Surface Charge Masking, J. Diabetes Sci Technol 2012; 6(4), pp. 755-563.
Pohl, et al., "Development of Ultra-Rapid-Acting Prandial Insulin analogs Requires Chelation of Zinc Ions and Charge Masking to Increase the Rate of Subcutaneous Absorption," available at http://files.shareholder.com/downloads/ BIOD/0x0x602912/3C955886-6AA4-4D66-BD33-3FFB4C906B25/EASD Poster September_2012_FINAL.pdf.
Krasner, et al., "Lispro Formulations BIOD-238 and BIOD-250 Associated With Faster Absorption and Declines From Peak Concentrations Compared to Humalog®" available at http://files.shareholder.com/downloads/ BIOD/2632769718x0x672700/BF867032-C746-4DB1-A80B-FFA9DE1E565B/Lispro_Formulations_BIOD-238_and_BIOD-250_Associated_With_Faster_Absorption_-ADA_Jun. 2013.PDF.
Capelle, M.A.H., et al., "High Throughput Screening of Protein Formulation Stability: Practical Considerations," European Journal of Pharmaceutics and Biopharmaceutics, vol. 65, No. 2, Jan. 5, 2007, pp. 131-148.
Patent Cooperation Treaty International Search Report and Written Opinion of the International Searching Authority pertaining to International Application No. PCT/US2015/064744; International Filing Date: Dec. 9, 2015; Date of Mailing: Mar. 23, 2016.
Prabhu, S., Jacknowitz, A. I., & Stout, P. J. (2001). A study of factors controlling dissolution kinetics of zinc complexed protein suspensions in various ionic species. International journal of pharmaceutics, 217(1), 71-78.
Patent Opposition Notice, Opposition 2018-700942, JP Patent 6328855, Nov. 22, 2018.
Description of Evidence, Opposition 2018-700942, JP Patent 6328855, Nov. 22, 2018.
Notice of Reasons for Revocation; Opposition 2018-700942, JP Patent 6328855, May 25, 2019.
https://web.archive.org/web/20120121064837/: rxlist.com: 80/humalog-drug.htm; Jan. 2012.
https://web.archive.org/web/20110526002304/http-//www.rxlist.com-80/humulin-r-drug.htm; May 2011.
A.Plum, et al., Pharmacokinetics of the Rapid-acting Insulin Analog, Insulin Aspart, in Rats, Dogs, and Pigs, and Pharmacodynamics of Insulin Aspart in Pigs, 2 Drug Metabolism and Disposition 28, p. 155-160 (2000).

* cited by examiner

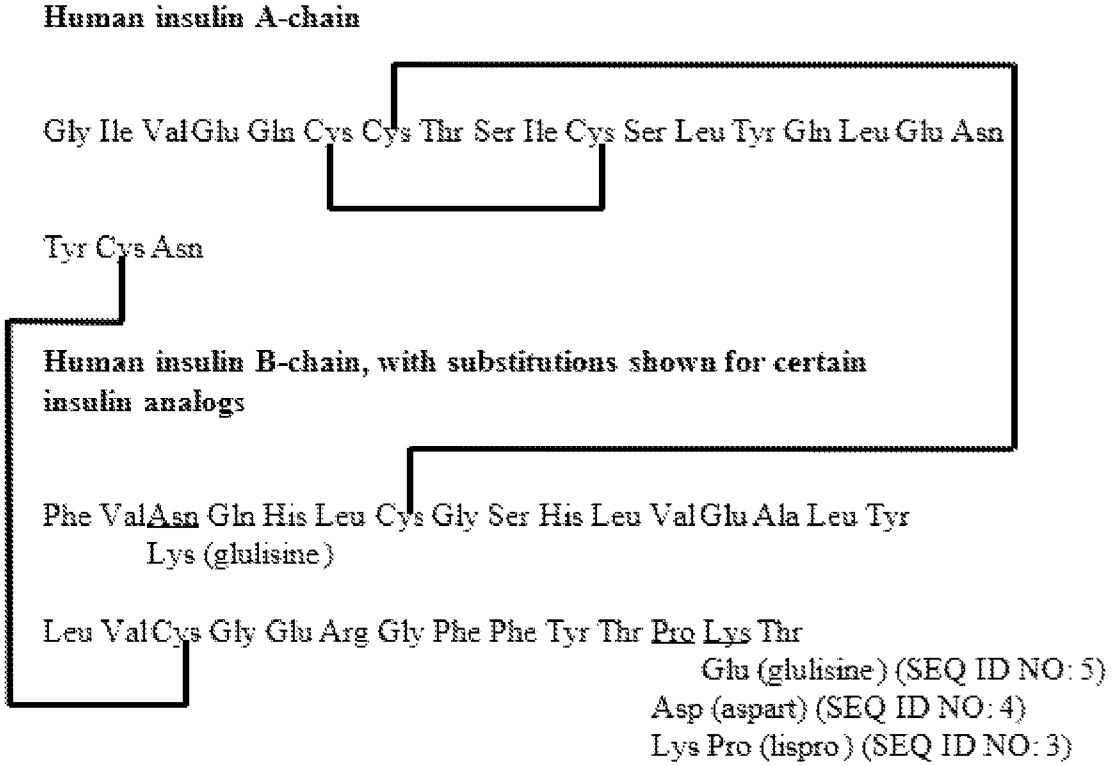
Human insulin A-chain
Gly Ile Val Glu Gln Cys Cys Thr Ser Ile Cys Ser Leu Tyr Gln Leu Glu Asn
Tyr Cys Asn
Human insulin B-chain, with substitutions shown for certain insulin analogs
Phe Val Asn Gln His Leu Cys Gly Ser His Leu Val Glu Ala Leu Tyr
Lys (glulisine)
Leu Val Cys Gly Glu Arg Gly Phe Phe Tyr Thr Pro Lys Thr
Glu (glulisine) (SEQ ID NO: 5)
Asp (aspart) (SEQ ID NO: 4)
Lys Pro (lispro) (SEQ ID NO: 3)

URI AGONIST/VASODILATOR

The present disclosure contains a Sequence Listing XML, which has been submitted electronically and is hereby incorporated by reference. The Sequence Listing XML is provided as a file titled "Sequence_Listing_XML_ST26_X20221C_000.xml", created on Feb. 19, 2024, and is 6.43 kilobytes in size.

The present invention is a pharmaceutical insulin composition for use in the treatment of diabetes to counteract post-prandial blood glucose excursions and for acute treatment of hyperglycemia. The composition includes human insulin or an insulin analog, and specific concentrations of citrate, chloride, in some cases including the addition of sodium chloride, zinc and, optionally, magnesium chloride and/or surfactant. The composition has a faster uptake of insulin from injection sites than existing commercial insulin compositions. The composition is useful for providing meal-time insulin activity or an acute treatment for hyperglycemia when insulin is needed.

The time-action profile of insulin is important for controlling post-prandial blood glucose levels. In healthy individuals, the pancreas secretes a spike of insulin in response to absorbed food, which results in increased blood insulin levels within several minutes. In individuals with type 1 diabetes and in certain individuals with type 2 diabetes, insulin must be administered. However, administered insulin enters blood slowly. Inadequate release of insulin and onset which is too slow at the beginning of a meal leads to hyperglycemia during or immediately after the meal. Too long duration of action and excessive insulin between meals causes postprandial hypoglycemia.

There have been previous efforts to reduce the time-action of insulin products. Early efforts to develop such products included the development of novel "rapid-acting" insulin analogs, like insulin lispro (HUMALOG®), insulin aspart (NOVOLOG®), and insulin glulisine (APIDRA®). Insulin lispro and insulin aspart achieve rapid action through changes in the amino acid sequences from the sequences of the amino acid chains in human insulin. Insulin glulisine also includes changes in the sequences of the amino acid chains in human insulin, and also lacks zinc and does not form stabilizing hexamers. The rapid-acting insulin analogs became available in the 1990s and early 2000s. Even with so-called rapid-acting insulin analogs, however, the maximum insulin level is not reached until 50-90 minutes following the injection. This is slower than insulin is released by a normally functioning pancreas and does not always match carbohydrate absorption profiles.

Another avenue to achieve rapid action that has been explored is the use of ingredients or excipients which improve the time action profile of insulin when provided in combination with insulin.

For example, US2013/0231281 discloses aqueous compositions comprising an insulin and particular oligosaccharides, either alone or in combination with a polyanionic compound. The polyanionic compound is an anionic polymer selected from the group consisting of selected from the group consisting of dextranmethylcarboxylic acid, polyglutamic acid, polyaspartic acid, PAA (polyacrylic acid), alginate, hyaluronic acid, polymers based on glucuronic acid or based on galacturonic acid and their salts, or is an anionic compound selected from the group consisting of citric acid, aspartic acid, glutamic acid, malic acid, tartaric acid, succinic acid, adipic acid, oxalic acid, triphosphate, polyphosphate, and their salts. In one embodiment, the polyanionic compound is sodium citrate. The polyanionic compounds are said to improve the performance of the oligosaccharide-containing compositions even when the oligosaccharide alone or the polyanionic compound alone has no effect on time action. No insulin time action results for compositions containing citrate but lacking an oligosaccharide are disclosed.

In addition, US2012/0178675 and US2014/0113856 disclose compositions containing insulin in combination with a zinc chelator such as ethylenediaminetetraacetic acid (EDTA) and what are described as "dissolution/stabilization" agents, such as citric acid or sodium citrate. US2014/0113856 states that early clinical trials on such compositions showed injection site discomfort, and purports to increase injection site tolerability through the addition of a magnesium containing compound. Such magnesium compounds include inorganic salts, such as magnesium hydroxide, magnesium sulfate, magnesium chloride, magnesium bromide, magnesium iodide, magnesium pyrophosphate, magnesium sulfate heptahydrate and magnesium oxide; and organic salts, such as magnesium EDTA, magnesium lactate, magnesium aspartate, magnesium acetate, magnesium carbonate, magnesium citrate, and magnesium gluconate. US2012/0178675 and US2014/0113856 did not disclose insulin time action results for compositions containing citric acid or citrate but not containing EDTA. A 2012 poster by the assignee of those applications, however, did compare the time action profile of an insulin lispro composition containing citrate and no EDTA to compositions containing varying concentrations of EDTA and citrate, and that poster states that "[c]itrate alone in the formulation is insufficient to improve the [insulin lispro] absorption profile;" and that "[b]oth chelation of zinc with EDTA (to hasten disassembly of the less stable insulin analog hexamer) and citrate (to mask the surface charge and prevent re-aggregation) are required above a threshold concentration to enhance the subcutaneous rate of absorption." Roderike Pohl, et al., "Development of Ultra-Rapid-Acting Prandial Insulin Analogs Requires Chelation of Zinc Ions and Charge Masking to Increase the Rate of Subcutaneous Absorption," available at http://files.shareholder.com/downloads/BIOD/3315705516x0x602912/3C955886-6AA4-4D66-BD33-3FFB4C906B25/EASD_Poster_September_2012_FINAL.pdf.

US2015/0065423 describes compositions comprising a peptide and a vasodilatory agent (e.g., nitroglycerin) and, optionally, what are described as "charge masking agents," such as citrate, a diketopiperazine, a diketopiperazine derivative, EDTA, di-arginine piperazine, a diarginine piperazine salt, a di-arginine piperazine isomer, a di-arginine piperazine ester and any combination thereof. No compositions containing citrate but lacking a vasodilatory agent are disclosed.

The prior art collectively does not teach an ultra-rapid insulin formulation with the excipients and specific concentrations thereof included in the present invention.

Despite the efforts described above, there remains a need for insulin compositions, intended for use at meal-time, that have more rapid uptake of insulin into the blood from the injection site; more rapid onset of action than existing insulin products; and chemical and physical stability during storage. The present invention seeks to provide compositions which meet these needs.

The present inventors have surprisingly found that compositions containing certain concentrations of citrate have more rapid uptake of insulin into the blood and/or onset of action than existing commercially available insulin compositions. The chemical and physical stability of the compositions under certain conditions is maintained, without eliminating the improvements in time action, by including in the compositions certain concentrations of stabilizing agents, such as zinc, sodium chloride, and, optionally, magnesium chloride and/or surfactant.

Accordingly, the present invention provides pharmaceutical compositions comprising insulin in a concentration of about 100 to about 200 IU/mL, citrate in a concentration of about 15 to about 35 mM, zinc in a concentration of about 0.2 to about 0.8 mM, and a preservative. In certain embodiments, the pharmaceutical compositions further comprise magnesium chloride in a concentration of up to about 5 mM.

In another embodiment, the present provides generally compositions comprising an insulin and specific concentrations of citrate and stabilizing agents.

In certain embodiments, the present invention provides pharmaceutical compositions comprising an insulin; citrate, in a concentration from about 10 to about 30 mM; zinc, in a concentration from about 0.2 to about 2 mM; magnesium, in a concentration from about 1 to about 15 mM; total chloride in a concentration from about 10 to about 60 mM; a surfactant, in a concentration from about 0.001 to about 0.2% w/v; and a preservative.

In certain embodiments, the present invention provides pharmaceutical compositions comprising an insulin; citrate, in a concentration from about 10 to about 30 mM; zinc, in a concentration from about 0.2 to about 2 mM; magnesium, in a concentration from about 1 to about 15 mM; sodium chloride in a concentration from about 1 to about 50 mM; a surfactant, in a concentration from about 0.001 to about 0.2% w/v; and a preservative.

In certain embodiments, pharmaceutical compositions of the present invention comprise insulin lispro, in a concentration from about 100 to about 500 IU/mL; citrate, in a concentration from about 10 to about 25 mM; magnesium, in a concentration of about 2 to about 9 mM; zinc, in a concentration from about 0.3 to about 1.3 mM; total chloride, in a concentration from about 15 to about 35 mM; poloxamer 188, in a concentration from about 0.03 to about 0.12% w/v; and metacresol, in a concentration of about 2.8 to about 3.5 mg/mL; and wherein the pH of the composition is from about 7.0 to 7.8.

In certain embodiments, pharmaceutical compositions of the present invention comprise insulin lispro, in a concentration from about 100 to about 500 IU/mL; citrate, in a concentration from about 10 to about 25 mM; magnesium, in a concentration of about 2 to about 9 mM; zinc, in a concentration from about 0.3 to about 1.3 mM; sodium chloride, in a concentration from about 1 to about 25 mM; poloxamer 188, in a concentration from about 0.03 to about 0.12% w/v; and metacresol, in a concentration of about 2.8 to about 3.5 mg/mL; and wherein the pH of the composition is from about 7.0 to 7.8.

In certain embodiments, pharmaceutical compositions of the present invention comprise insulin lispro, in a concentration from about 100 to about 200 IU/mL; citrate, in a concentration from about 15 to about 25 mM; magnesium chloride, in a concentration of about 3 to about 8 mM; zinc, in a concentration from about 0.3 to about 1.1 mM; total chloride, in a concentration from about 20 to about 25 mM; poloxamer 188, in a concentration from about 0.06 to about 0.09% w/v; and metacresol, in a concentration of about 2.8 to about 3.5 mg/mL; and wherein the pH of the composition is from about 7.0 to 7.8.

In certain embodiments, pharmaceutical compositions of the present invention comprise insulin lispro, in a concentration from about 100 to about 200 IU/mL; citrate, in a concentration from about 15 to about 25 mM; magnesium chloride, in a concentration of about 3 to about 8 mM; zinc, in a concentration from about 0.3 to about 1.1 mM; sodium chloride, in a concentration from about 1 to about 20 mM; poloxamer 188, in a concentration from about 0.06 to about 0.09% w/v; and metacresol, in a concentration of about 2.8 to about 3.5 mg/mL; and wherein the pH of the composition is from about 7.0 to 7.8.

In certain embodiments, pharmaceutical compositions of the present invention comprise insulin lispro, in a concentration from about 100 to about 200 IU/mL; citrate, in a concentration from about 15 to about 25 mM; magnesium chloride, in a concentration of about 3 to about 8 mM; zinc, in a concentration from about 0.6 to about 1.1 mM; total chloride, in a concentration from about 20 to about 25 mM; poloxamer 188, in a concentration from about 0.06 to about 0.09% w/v; and metacresol, in a concentration of about 2.8 to about 3.5 mg/mL; and wherein the pH of the composition is from about 7.0 to 7.8.

In certain embodiments, pharmaceutical compositions of the present invention comprise insulin lispro, in a concentration from about 100 to about 200 IU/mL; citrate, in a concentration from about 15 to about 25 mM; magnesium chloride, in a concentration of about 3 to about 8 mM; zinc, in a concentration from about 0.6 to about 1.1 mM; sodium chloride, in a concentration from about 1 to about 20 mM; poloxamer 188, in a concentration from about 0.06 to about 0.09% w/v; and metacresol, in a concentration of about 2.8 to about 3.5 mg/mL; and wherein the pH of the composition is from about 7.0 to 7.8.

In certain embodiments, pharmaceutical compositions of the present invention comprise insulin lispro, in a concentration of 100 IU/mL; citrate, in a concentration of about 25 mM; zinc, in a concentration of about 0.6 to about 0.9 mM; magnesium chloride, in a concentration of about 5 mM; total chloride, in a concentration of about 20 to about 25 mM; poloxamer 188, in a concentration of about 0.09% w/v; and metacresol, in a concentration of about 3.15 mg/mL; and wherein the pH of the composition is about 7.4.

In certain embodiments, pharmaceutical compositions of the present invention comprise insulin lispro, in a concentration of 100 IU/mL; citrate, in a concentration of about 25 mM; zinc, in a concentration of about 0.6 to about 0.9 mM; magnesium chloride, in a concentration of about 5 mM; sodium chloride, in a concentration of about 1 to about 20 mM; poloxamer 188, in a concentration of about 0.09% w/v; and metacresol, in a concentration of about 3.15 mg/mL; and wherein the pH of the composition is about 7.4.

In certain embodiments, pharmaceutical compositions of the present invention comprise insulin lispro, in a concentration of 100 IU/mL; citrate, in a concentration of about 25 mM; zinc, in a concentration of about 0.9 mM; magnesium chloride, in a concentration of about 5 mM; total chloride, in a concentration of about 20-25 mM; poloxamer 188, in a concentration of about 0.09% w/v; and metacresol, in a concentration of about 3.15 mg/mL; and wherein the pH of the composition is about 7.4.

In certain embodiments, pharmaceutical compositions of the present invention comprise insulin lispro, in a concentration of 100 IU/mL; citrate, in a concentration of about 25 mM; zinc, in a concentration of about 0.9 mM; magnesium chloride, in a concentration of about 5 mM; sodium chloride, in a concentration of about 1 to about 20 mM; poloxamer 188, in a concentration of about 0.09% w/v; and metacresol, in a concentration of about 3.15 mg/mL; and wherein the pH of the composition is about 7.4.

In certain embodiments, pharmaceutical compositions of the present invention comprise insulin lispro, in a concentration of about 200 IU/mL; citrate, in a concentration from about 15 to about 25 mM; magnesium chloride, in a concentration of about 3 to about 8 mM; zinc, in a concentration from about 0.8 to about 1.1 mM; total chloride, in a concentration from about 20 to about 25 mM; poloxamer 188, in a concentration from about 0.06 to about 0.09% w/v; and metacresol, in a concentration of about 2.8 to about 3.5 mg/mL; and wherein the pH of the composition is from about 7.0 to 7.8.

In certain embodiments, pharmaceutical compositions of the present invention comprise insulin lispro, in a concentration of about 200 IU/mL; citrate, in a concentration from about 15 to about 25 mM; magnesium chloride, in a concentration of about 3 to about 8 mM; zinc, in a concentration from about 0.8 to about 1.1 mM; sodium chloride, in a concentration from about 1 to about 20 mM; poloxamer 188, in a concentration from about 0.06 to about 0.09% w/v; and metacresol, in a concentration of about 2.8 to about 3.5 mg/mL; and wherein the pH of the composition is from about 7.0 to 7.8.

In addition, the present invention also provides a method of treating diabetes comprising administering to a human in need thereof an effective dose of a pharmaceutical composition of the present invention.

In addition, the present invention provides a pharmaceutical composition of the present invention for use in therapy. More particularly, the present invention provides a pharmaceutical composition of the present invention for use in the treatment of diabetes. The present invention also provides the use of a pharmaceutical composition of the present invention in the manufacture of a medicament for the treatment of diabetes.

In addition, the present invention provides an article of manufacture comprising a pharmaceutical composition of the present invention. In particular, the present invention provides an article of manufacture comprising a pharmaceutical composition of the present invention wherein the article of manufacture is a multi-use vial. In particular, the present invention provides an article of manufacture comprising a pharmaceutical composition of the present invention wherein the article of manufacture is a re-usable pen injector. In particular, the present invention provides an article of manufacture comprising a pharmaceutical composition of the present invention wherein the article of manufacture is a pump device for continuous subcutaneous insulin infusion therapy.

In an embodiment, the insulin is selected from the group consisting of human insulin, or a rapid-acting structural variant, mutant, or analog of human insulin, such as insulin lispro, insulin aspart or insulin glulisine. In a preferred embodiment, the insulin is insulin lispro.

In an embodiment, the preservative is selected from the group consisting of phenol and meta-cresol. Preferably, the preservative is meta-cresol. In an embodiment, the meta-cresol concentration is from about 2.5 mg/mL to about 3.8 mg/mL. Preferably, the meta-cresol concentration is about 3.15 mg/mL.

In an embodiment, the composition further comprises a tonicity agent. In an embodiment, the tonicity agent is glycerol. In certain embodiments, the glycerol concentration is from about 1 to about 16 mg/mL.

In an embodiment, the composition further comprises a buffer. In certain embodiments, the buffer is sodium phosphate.

In certain embodiments the composition further comprises an additional stabilizing agent. In certain embodiments the composition further comprises a surfactant.

In certain embodiments, the composition does not include any additional chelating agent, such as EDTA, any additional vasodilatory agent, such as nitroglycerin, and/or any oligosaccharides.

In an embodiment, the pH of the composition is from about 7.0 to about 7.8. In certain preferred embodiments, the pH of the composition is from about 7.3 to about 7.5. In certain preferred embodiments, the pH of the composition is about 7.4.

In certain embodiments, the pharmaceutical composition provides for an uptake of insulin into the blood and/or onset of action that is at least 10%, at least 20%, at least 30%, at least 40%, or at least 50% more rapid than for compositions of rapid-acting insulin analogs which do not contain citrate, when measured by one or more pharmacokinetic or pharmacodynamic parameters relevant to time action, such as: time to maximum insulin concentration (Tmax); time to reach one half of the maximum insulin concentration (early ½ Tmax); time to reach one half of the maximum insulin concentration during the declining phase of the concentration-over-time curve (late ½ Tmax); time between early and late ½ Tmax (Tmax spread); percentage of total insulin dose absorbed at different times based on fractional area under the insulin concentration curve (e.g., $AUC_{0\text{-}30\ min}$, $AUC_{0\text{-}60\ min}$, $AUC_{0\text{-}120\ min}$, $AUC_{0\text{-}180\ min}$); time to reach one half of the total insulin concentration (T50); time to reach maximal glucose infusion rate (GIRmax), time to reach one half of the maximum glucose infusion rate (early ½ GIRmax); time to reach one half of the maximum glucose infusion rate during the declining phase of the concentration-over-time curve (late ½ GIRmax); percentage of total glucose infused at different times based on fractional area under the GIR curve (e.g., $GIR_{0\text{-}30\ min}$, $GIR_{0\text{-}60\ min}$, $GIR_{0\text{-}120\ min}$, $GIR_{0\text{-}180\ min}$).

In certain embodiments, the pharmaceutical composition provides for an uptake of insulin into the blood and/or onset of action that is between 10% and 50% more rapid than for compositions of rapid-acting insulin analogs which do not contain citrate, when measured by one or more pharmacokinetic or pharmacodynamic parameters relevant to time action, such as those described above.

In certain embodiments, the pharmaceutical composition is stable to allow for storage of at least 24 months at 2-8° C. In certain embodiments, the pharmaceutical composition is stable to allow for up to 28 days in-use at temperatures of up to 30° C. for vials or cartridges in re-usable pen injectors. In certain embodiments, the pharmaceutical composition is stable to allow for storage of at least 36 months at 2-8° C. In certain embodiments, the pharmaceutical composition is stable to allow for up to 32 days in-use at temperatures of up to 30° C. for vials or cartridges in re-usable pen injectors. In certain embodiments, the composition is stable to allow for use in a pump device for continuous subcutaneous insulin infusion therapy for up to 7 days.

In an embodiment, the pharmaceutical composition comprises insulin lispro, in a concentration of about 100 IU/mL; citrate, in a concentration of about 15 mM; zinc, in a concentration of about 0.3 mM; sodium chloride, in a concentration of about 15 mM; magnesium chloride, in a concentration of about 5 mM; metacresol, in a concentration of about 3.15 mg/mL; and glycerol, in a concentration of about 7.6 mg/mL.

In another embodiment, the pharmaceutical composition comprises insulin lispro, in a concentration of about 100 IU/mL; citrate, in a concentration of about 25 mM; zinc, in a concentration of about 0.3 mM; sodium chloride, in a concentration of about 15 mM; magnesium chloride, in a concentration of about 5 mM; metacresol, in a concentration of about 3.15 mg/mL; and glycerol, in a concentration of about 4.5 mg/mL.

In another embodiment, the pharmaceutical composition comprises insulin lispro, in a concentration of about 100 IU/mL; citrate, in a concentration of about 35 mM; zinc, in a concentration of about 0.3 mM; sodium chloride, in a concentration of about 23 mM; magnesium chloride, in a concentration of about 5 mM; and metacresol, in a concentration of about 3.15 mg/mL.

In another embodiment, the pharmaceutical composition comprises insulin lispro, in a concentration of about 100 IU/mL; citrate, in a concentration of about 25 mM; zinc, in a concentration of about 0.3 mM; sodium chloride, in a concentration of about 25 mM; and metacresol, in a concentration of about 3.15 mg/mL.

In another embodiment, the pharmaceutical composition comprises insulin lispro, in a concentration of about 100 IU/mL; citrate, in a concentration of about 15 mM; zinc, in a concentration of about 0.3 mM; sodium chloride, in a concentration of about 15 mM; magnesium chloride, in a concentration of about 5 mM; metacresol, in a concentration of about 3.15 mg/mL; and glycerol, in a concentration of about 7.6 mg/mL; and wherein the pharmaceutical composition provides for an uptake of insulin into the blood and/or onset of action that is between 10% and 20%, between 20% and 30%, between 30% and 40% or between 40% and 50% more rapid than for compositions of rapid-acting insulin analogs which do not contain citrate, when measured by one or more pharmacokinetic or pharmacodynamic parameters relevant to time action, such as those described above.

In another embodiment, the pharmaceutical composition comprises insulin lispro, in a concentration of about 100 IU/mL; citrate, in a concentration of about 25 mM; zinc, in a concentration of about 0.3 mM; sodium chloride, in a concentration of about 15 mM; magnesium chloride, in a concentration of about 5 mM; metacresol, in a concentration of about 3.15 mg/mL; and glycerol, in a concentration of about 4.5 mg/mL; and wherein the pharmaceutical composition provides for an uptake of insulin into the blood and/or onset of action that is between 10% and 50% more rapid than for compositions of rapid-acting insulin analogs which do not contain citrate, when measured by one or more pharmacokinetic or pharmacodynamic parameters relevant to time action, such as those described above.

In another embodiment, the pharmaceutical composition comprises insulin lispro, in a concentration of about 100 IU/mL; citrate, in a concentration of about 35 mM; zinc, in a concentration of about 0.3 mM; sodium chloride, in a concentration of about 23 mM; magnesium chloride, in a concentration of about 5 mM; and metacresol, in a concentration of about 3.15 mg/mL; and wherein the pharmaceutical composition provides for an uptake of insulin into the blood and/or onset of action that is between 10% and 50% more rapid than for compositions of rapid-acting insulin analogs which do not contain citrate, when measured by one or more pharmacokinetic or pharmacodynamic parameters relevant to time action, such as those described above.

In another embodiment, the pharmaceutical composition comprises insulin lispro, in a concentration of about 100 IU/mL; citrate, in a concentration of about 25 mM; zinc, in a concentration of about 0.3 mM; sodium chloride, in a concentration of about 25 mM; and metacresol, in a concentration of about 3.15 mg/mL; and wherein the pharmaceutical composition provides for an uptake of insulin into the blood and/or onset of action that is between 10% and 50% more rapid than for compositions of rapid-acting insulin analogs which do not contain citrate, when measured by one or more pharmacokinetic or pharmacodynamic parameters relevant to time action, such as those described above.

FIG. 1 depicts the amino acid sequences and disulfide bonds of human insulin and of the rapid-acting insulin that are presently approved for use in treating meal-time excursions of blood glucose.

When used herein, the term "composition" refers to a combination of insulin and the other ingredients or excipients wherein the insulin and other ingredients or excipients are combined in a single combined formulation.

When used herein, "insulin" means human insulin or a rapid-acting structural variant, mutant, or analog of human insulin that has the functional activity of but faster onset of action than human insulin. Particular rapid-acting analogs of human insulin are insulin lispro, insulin aspart, and insulin glulisine. Insulin for commercial products may be produced using recombinant DNA methods or by chemical synthesis. Recombinant methods are well-known and are strongly preferred. A molecule of human insulin (CAS No. 11061-68-0) consists of two amino acid chains, A and B, whose sequences are well-known.

The human insulin A-chain has the following sequence of amino acids:

```
                                    (SEQ ID NO: 1)
Gly Ile Val Glu Gln Cys Cys Thr Ser Ile Cys Ser

Leu Tyr Gln Leu Glu Asn Tyr Cys Asn.
```

The human insulin B-chain has the following sequence of amino acids:

```
                                    (SEQ ID NO: 2)
Phe Val Asn Gln His Leu Cys Gly Ser His Leu Val

Glu Ala Leu Tyr Leu Val Cys Gly Glu Arg Gly Phe

Phe Tyr Thr Pro Lys Thr.
```

The chains are joined by two disulfide bonds: CysA7-CysB7 and CysA20-CysB19. The A-chain has an intra-chain disulfide bond at CysA6-CysA11. Human insulin has the empirical formula $C_{257}H_{383}N_{65}O_{77}S_6$ and a molecular weight of 5808.

Insulin lispro, the drug substance in HUMALOG®, is identical to human insulin in terms of its primary amino acid sequence except for an inversion of the natural proline-lysine sequence on the B-chain at positions 28 and 29 ($28^B$-L-Lysine-$29^B$-L-proline human insulin). Insulin lispro (CAS No. 133107-64-9) has been shown to be equipotent to human insulin on a molar basis but its effect after subcutaneous injection is more rapid and of shorter duration than that of injected soluble human insulin. HUMALOG® contains m-cresol as a preservative and a stabilizer agent, a tonicity modifier (glycerol), a buffering agent (dibasic sodium phosphate), a stabilizer (zinc oxide) and pH adjustment for the vehicle.

A molecule of insulin lispro consists of the human insulin A-chain (SEQ ID NO. 1) cross-linked with the insulin lispro B-chain, whose amino acid sequence is given by SEQ ID NO:3, below:

(SEQ ID NO: 3)
Phe Val Asn Gln His Leu Cys Gly Ser His Leu Val

Glu Ala Leu Tyr Leu Val Cys Gly Glu Arg Gly Phe

Phe Tyr Thr Lys Pro Thr.

The chemical formula of insulin lispro is $C_{257}H_{383}N_{65}O_{77}S_6$ and its molecular weight is approximately 5808. One unit of insulin lispro is equivalent to 0.0347 mg insulin lispro.

Insulin aspart (CAS No. 116094-23-6), the drug substance in NOVOLOG®, is another rapid-onset insulin analog. Its structure consists of the A-chain of human insulin (SEQ ID NO. 1) and a B-chain in which the Pro at B28 is replaced with Asp (Pro-B28-Asp human insulin), as reflected in the following amino acid sequence:

(SEQ ID NO: 4)
Phe Val Asn Gln His Leu Cys Gly Ser His Leu Val

Glu Ala Leu Tyr Leu Val Cys Gly Glu Arg Gly Phe

Phe Tyr Thr Asp Lys Thr.

Insulin aspart ($28^B$ aspartic acid-human insulin) has the empirical formula $C_{256}H_{381}N_{65}O_{79}S_6$ and a molecular weight of about 5826. One unit of insulin aspart corresponds to 6 nmol, corresponding with 0.035 mg salt-free anhydrous insulin aspart. Insulin glulisine (CAS No. 207748-29-6), the drug substance in APIDRA®, is yet another rapid-onset insulin analog. A molecule of insulin glulisine consists of human insulin A-chain (SEQ ID NO. 1) and a modified B-chain (Asn-B3-Lys, Lys-B29-Glu) compared with human insulin, as reflected in the following amino acid sequence: Phe Val Lys Gln His Leu Cys Gly Ser His Leu Val Glu Ala Leu Tyr Leu Val Cys Gly Glu Arg Gly Phe Phe Tyr Thr Pro Glu Thr (SEQ ID NO: 5).

Insulin glulisine ($3^B$-lysine-$29^B$-glutamic acid-human insulin) has the empirical formula $C_{258}H_{384}N_{64}O_{78}S_6$ and a molecular weight of 5823. One unit of insulin glulisine corresponds approximately to 0.0349 mg of insulin glulisine.

The following scheme depicts the amino acid sequences and disulfide bonds of human insulin and of the rapid-acting insulin analogs that are presently approved for use in treating meal-time excursions of blood glucose:

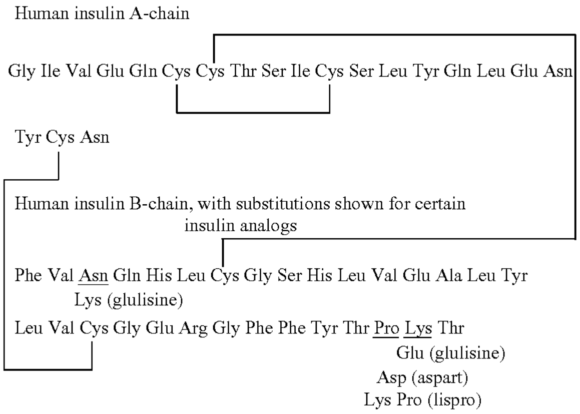

In certain embodiments, the compositions of the present invention have concentrations of insulin from about 100 to about 500 IU/mL. In certain embodiments, the compositions of the present invention have concentrations of insulin from about 100 to about 300 IU/mL. In certain embodiments, the compositions of the present invention have concentrations of insulin from about 100 to about 200 IU/mL. Certain compositions comprise about 100 IU/mL. Certain compositions comprise about 200 IU/mL.

The improvements in the time action profile of the above-referenced insulin analogs demonstrated in the present invention are achieved through the use of certain specific concentrations of citrate and without the need for any additional chelating agent, such as those described in US2012/0178675 and US2014/0113856 (e.g., EDTA), any additional vasodilatory agent, such as those described in US2015/0065423 (e.g., nitroglycerin), or any other oligosaccharides, such as those described in US2013/0231281.

The citrate ion has the chemical name 2-hydroxypropane-1,2,3-tricarboxylate, molecular formula $C_6H_5O_7^{-3}$, and molecular weight of 189. The citrate ion is widely distributed in plants and animals and is a naturally occurring component of the diet. It is a common metabolite in oxidative metabolism and an important component of bone. A number of citrates are GRAS (generally regarded as safe) by the U.S. Food and Drug Administration for use in foods, including the following:

| GRAS Substance | Formula (m.w.) | CAS No. | 21 CFR |
|---|---|---|---|
| Citric acid | $C_6H_8O_7$ (192.12) | 77-92-9 | 184.1033 |
| Sodium citrate | $C_6H_5Na_3O_7$ (258.07) | 68-04-2 | 184.1751 |
| Potassium citrate monohydrate | $C_6H_5O_7K_3$ (324.41) | 6100-05-6 | 184.1625 |

Various citrate-containing compounds are also included as ingredients in parenteral drug products according to the U.S. Food and Drug Administration Inactive Ingredients database, including for example, citric acid, citric acid monohydrate, citric acid anhydrous, sodium citrate, anhydrous trisodium citrate, trisodium citrate dihydrate. The particular citrate compound used in the compositions of the present invention may be the acidic form or various salt forms, especially the alkali (e.g., sodium and potassium) salts and/or mono or dihydrates thereof. Of these, sodium citrate is preferred. In some embodiments, the concentration of citrate in the compositions of the present invention ranges from about 10 to about 35 mM or about 15 mM to about 35. In preferred embodiments, the concentration of citrate ranges from about 10 to about 30 mM or about 15 to about 30 mM. In certain preferred embodiments, the concentration of citrate ranges from about 15 to about 25 mM. In certain embodiments, the concentration of citrate ranges from about 15 to about 25 mM. In certain embodiments, the concentration of citrate ranges from about 15 to about 20 or about 20 to about 25 mM. Certain compositions have citrate concentrations of about 15, about 20, about 25, about 30 or 35 mM.

Although the addition of citrate has been found to result in improvements in time action, the addition of citrate also leads to greater liabilities from a stability standpoint. Thus, in order to have sufficient chemical and physical stability for long-term storage and use, the compositions of the present invention further comprise contain stabilizing agents, such as zinc, magnesium, chloride and surfactant(s).

Zinc oxide may be added to provide the desired stoichiometry of zinc ions. Insulin hexamers have 2 specific, high affinity zinc binding sites. Zinc ions incorporated into such hexamers are sometimes referred to as “bound” zinc. Currently available zinc-containing formulations include between about 2 and 4 zinc ions per hexamer of insulin. Some commercial insulin compositions have about 2.4 ions of zinc per six molecules of insulin (HUMULIN® R U-500), and some have about 3.0 ions of zinc per six molecules of insulin (HUMALOG®, NOVOLOG®). The 100 U/mL formulations of insulin lispro (HUMALOG®) and insulin aspart (NOVOLOG®) have about 3.0 ions of zinc per six molecules of insulin, which corresponds with a concentration of about 0.3 mM. The currently available 200 U/mL formulation of HUMALOG® has about 3.5 ions of zinc per six molecules of insulin, which corresponds with a zinc concentration of about 0.7 mM. The currently available 100 U/mL formulation of human insulin sold by Eli Lilly and Company (HUMULIN® R) contains about 2.3 ions of zinc per six molecules of insulin, which corresponds with a zinc concentration of about 0.23 mM.

The compositions of the present invention have a zinc concentration sufficient to provide at least enough zinc ions for the insulin molecules to form stabilizing hexamers. Thus, the compositions of the present invention must include sufficient zinc to provide at least 2 ions of zinc per hexamer of insulin. The compositions of certain embodiments of the present invention have a zinc concentration from about 0.2 mM to about 0.8 mM. When the insulin concentration is 100 IU/mL, the zinc concentration in certain embodiments of the present invention is about 0.3 mM (about 3.0 Zn ions/six insulin molecules). In certain embodiments of the present invention having, for example, insulin concentrations of about 100 U/mL, about 200 U/mL, about 300 U/mL or about 500 U/mL, the minimum zinc concentration necessary to provide 2 ions of zinc per insulin hexamer would be about 0.2 mM, about 0.4 mM, about 0.6 mM or about 1 mM, respectively.

The inclusion of excess zinc—i.e., more zinc than would be bound in insulin hexamers—may be used to further stabilize compositions of the present invention. Such zinc is sometimes referred to as “free” or “unbound” zinc. In certain compositions of the present invention, the inclusion of excess free or unbound zinc has been found to have a stabilizing effect. Compositions having 100 about U/mL of insulin lispro and zinc concentrations up to about 1 mM—which would constitute about 0.2 mM bound and about 0.8 mM unbound or free zinc—have been found to be both fast acting and stable. The inclusion of too much free or unbound zinc, however, may attenuate the improvements in time action. For example, a composition having about 100 U/mL of insulin lispro with a zinc concentration of about 5 mM—which would constitute about 4.8 mM unbound zinc—was found to not have the improvements in time action seen in compositions with lower zinc concentrations. In certain embodiments of the present invention, the concentration of zinc ranges from about 0.2 to about 2 mM, about 0.4 to about 1 mM, or about 0.6 to about 0.9 mM. In certain embodiments, the concentration of zinc is about 0.6, about 0.7, about 0.8 or about 0.9 mM.

The inclusion of magnesium ($Mg^{+2}$) in compositions of the present invention has also been found to have a stabilizing effect. Magnesium ions may be provided in a variety of manners, such as through the addition of magnesium chloride, which has a molecular formula of $MgCl_2$ and molecular weight of 95.211.

While magnesium may have stabilizing effects in certain compositions, concentrations which exceed the concentration of citrate will result in insulin precipitation. Thus, the maximum amount of magnesium that may be included is limited by the amount of citrate that is included. For example, when $MgCl_2$ is used a stabilizing agent in the compositions of the present invention, the molar ratio of magnesium to citrate ranges from about 1:10 to about 1:2. Preferably the molar ratio of magnesium chloride to citrate ranges from about 1:5 to about 1:3. Thus, for example, in order to achieve a molar ratio of magnesium to citrate from about 1:10 to about 1:2 in a composition wherein the citrate concentration is between about 10 to about 30 mM, the concentration of magnesium would be between about 1 and about 15 mM. Similarly, in order to achieve a molar ratio of magnesium to citrate of about 1:5 to about 1:3 in a composition wherein the citrate concentration is 25 mM, the concentration of magnesium would range from 5 to 8.3 mM. In certain embodiments, the concentration of magnesium ranges from about 1 about 15 mM. In certain embodiments, the concentration of magnesium ranges from about 1 about 5, about 5 to about 10 or about 10 to about 15 mM. The concentration of magnesium chloride in certain embodiments of the present invention ranges from 1 to about 5 mM (~0.48 mg/mL). In certain embodiments, the concentration of magnesium is about 5 mM.

The inclusion of certain concentrations of chloride ions ($Cl^-$) in compositions of the present invention has also been found to have a stabilizing effect. Chloride ions may be provided in a variety of manners, including through the use of $MgCl_2$ to provide magnesium, as described above, or through the addition of sodium chloride. The compositions of certain embodiments of the present invention comprise sodium chloride. The molecular formula of sodium chloride is NaCl and its molecular weight is 58.44. Sodium chloride is used in some currently available formulations of rapid acting insulin analogs, such as APIDRA® (insulin glulisine), which comprises 5 mg/mL sodium chloride, NOVOLOG® (insulin aspart), which comprises 0.58 mg/mL sodium chloride.

While the addition of certain quantities of chloride, e.g., through the inclusion in the composition of chloride-containing excipients such as $MgCl_2$ or NaCl, has been found to have a stabilizing effect, if the total chloride content of the composition is too high, the insulin in the composition may crystallize at low temperatures. Thus, the total chloride content of the composition must be taken into consideration.

In order to determine the total chloride content of a composition, one must take into consideration not just chloride ions which may be added to the composition through the addition of magnesium chloride and/or sodium chloride as stabilizing agents, but also through the addition of other components, for example with the insulin bulk active pharmaceutical ingredient (API), through the addition of small amounts of HCl which may be necessary for pH adjustments, and/or in connection with the provision of Zn, which may be added in the form of a solution prepared by solubilizing zinc oxide (ZnO) with HCl.

In certain embodiments, sodium chloride is used to provide the amount of additional chloride needed to reach the target chloride concentration or concentration range—i.e., the amount of sodium chloride to be added is determined by subtracting from the target chloride concentration the amount of chloride provided through the addition of other components, such as through the addition of insulin API, magnesium chloride and/or any HCl which might be necessary for pH adjustments and/or solubilization of zinc oxide. For example, if the target chloride concentration in a formulation is about 20 mM, and 15 mM of chloride is provided through a combination of the bulk insulin API, magnesium chloride, and HCl used for pH adjustments, 5 mM of sodium chloride must be added. Persons of skill in the art will understand that the quantity of sodium chloride to be added in such formulations may be determined either by: (1) prospectively calculating the amount of additional chloride that will be needed based on the theoretical chloride content added through other sources; or (2) preparing a formulation of all of the excipients except for sodium chloride, measuring the chloride content of that formulation, and calculating the difference between that amount and the targeted chloride concentration or concentration range. The chloride content of an aqueous formulation maybe measured using a variety of known techniques, such as by titration or ion-selective electrode methods.

In addition, the low temperature crystallization issues associated with relatively high chloride concentrations have also been found to be sensitive to citrate concentrations. Thus, compositions of the present invention having citrate concentrations at the lower end of the range provided for herein may be more tolerant of relatively higher chloride concentrations than compositions having citrate concentrations at the higher end of the range provided for herein. For example, the addition of sodium chloride concentrations as high as 50-75 mM to formulations containing 25 mM citrate have been observed to lead to low temperature crystallization issues, but such issues are not consistently observed either when 50 mM sodium chloride is added to a 15 mM citrate formulation or when 25 mM sodium chloride is added to a 25 mM citrate formulation.

For the sake of clarity, when used herein, the terms "chloride" or "total chloride" refer to the total amount of chloride ions in a composition provided in connection with the addition of any component, e.g., the source(s) of chloride ions in a composition which is stated to comprise 25 mM chloride or total chloride include any chloride provided through the addition of $MgCl_2$, NaCl and/or any HCl needed for pH adjustments or solubilization of ZnO. On the other hand, the terms "magnesium chloride," "$MgCl_2$," "sodium chloride" and "NaCl" refer to the amount of these particular salts that are added to a composition. Thus, in a composition which is described as comprising 5 mM magnesium chloride and 10 mM sodium chloride, for example, the concentration of chloride, or total chloride, includes the combined amount of chloride ions provided by the magnesium chloride, sodium chloride and any other source, such as HCl.

In certain embodiments of the present invention, the total chloride concentration ranges from about 10 to about 60 mM. In certain embodiments, the total chloride concentration ranges from about 15 to about 35 mM. In certain embodiments, the total chloride concentration ranges from about 20 to about 25 mM. In certain embodiments, the total chloride concentration is about 20 mM, about 21 mM, about 22 mM, about 23 mM, about 24 mM or about 25 mM.

In certain embodiments of the present invention, the composition comprises sodium chloride in a concentration ranging from about 1 to about 50 mM. In certain embodiments, the concentration of sodium chloride is from about 1 to about 25 mM. In certain embodiments, the concentration of sodium chloride ranges from about 1 to about 20 mM. The concentration of sodium chloride in certain embodiments of the present invention ranges from about 15 mM (~0.88 mg/mL) to about 25 mM (~2.0 mg/mL). In certain embodiments, the concentration of sodium chloride is about 1, about 2, about 3, about 4, about 5, about 6, about 7, about 8, about 9, about 10, about 11, about 12, about 13, about 14, about 15, about 16, about 17, about 18, about 19 or about 20 mM.

If necessary to achieve sufficient chemical and physical stability, the composition may further comprise one or more additional stabilizing agents. Exemplary stabilizing agents include surfactants. It has surprisingly been discovered that combinations of surfactant and magnesium as stabilizing agents may have greater-than-additive or synergistic stabilizing effects in compositions of the present invention.

Examples of surfactants disclosed for use in parenteral pharmaceutical compositions include polysorbates, such as polysorbate 20 (TWEEN® 20), polyethylene glycols such as PEG 400, PEG 3000, TRITON™M X-100, polyethylene glycols such as polyoxyethylene (23) lauryl ether (CAS Number: 9002-92-0, sold under trade name BRIJ®), alkoxylated fatty acids, such as MYRJ™, polypropylene glycols, block copolymers such as poloxamer 188 (CAS Number 9003-11-6, sold under trade name PLURONIC® F-68) and poloxamer 407 (PLURONIC® F127), sorbitan alkyl esters (e.g., SPAN®), polyethoxylated castor oil (e.g., KOLLIPHOR®, CREMOPHOR®) and trehalose and derivatives thereof, such as trehalose laurate ester. In certain embodiments, the surfactant is selected from the group consisting of polyoxyethylene (23) lauryl ether, poloxamer 188 and trehalose laurate ester. A preferred surfactant is poloxamer 188. In certain embodiments, the concentration of surfactant, such as poloxamer 188, ranges from about 0.001 to about 2% w/v, about 0.001 to about 0.2% w/v, about 0.03 to about 0.12% w/v, or about 0.06 to about 0.09% w/v. In certain embodiments, the concentration of poloxamer 188 is about 0.06, about 0.07, about 0.08 or about 0.09% w/v.

In addition, the compositions of the present invention include one or more preservatives, which provide anti-microbial properties and may further provide stability benefits. The compositions are sterile when first produced, however, when the composition is provided in a multi-use vial or cartridge, an anti-microbial preservative compound or mixture of compounds that is compatible with the other components of the formulation is typically added at sufficient strength to meet regulatory and pharmacopoeial anti-microbial preservative requirements. See U.S. Pharmacopeia Monographs. Insulin lispro injection. USP29-NF24; British Pharmacopeia Monographs 2008 Volume III: Insulin aspart injection; U.S. Pharmacopeia Monographs. Insulin assays; and U.S. Pharmacopeia general chapters. USP29-NF24. Rockville, MD: U.S. Pharmacopeial Convention; 2005. Antimicrobial effectiveness testing; pp. 2499-2500. Preferred preservatives are aryl acids and phenolic compounds, or mixtures of such compounds.

The compositions of the present invention thus include one or more preservatives. Effective concentrations can be ascertained readily using the methods referenced above. Preservatives commonly used in insulin products include phenol (CAS No. 108-95-2, molecular formula $C_6H_5OH$, molecular weight 94.11), and m-cresol (CAS No. 108-39-4, molecular formula $C_7H_8O$, molecular weight 108.14). Present commercial compositions, for example, contain 3.15 mg/mL m-cresol (HUMALOG® and APIDRA®), 1.72 mg/mL m-cresol and 1.50 mg/mL phenol (NOVOLOG®), and 2.5 mg/mL m-cresol (HUMULIN® R U-500). The compositions of the present invention include one or more preservatives. In an embodiment the preservative is selected from the group consisting of phenol and metacresol and mixtures thereof. Preferably the preservative is metacresol. In certain embodiments the metacresol concentration is from about 2.5 mg/mL to about 3.8 mg/mL. Preferably the concentration of metacresol is about 3.15 mg/mL.

It is desirable to approximately match the tonicity (i.e., osmolality) of body fluids at the injection site as closely as possible when administering the compositions because solutions that are not approximately isotonic with body fluids can produce a painful stinging sensation when administered. Thus, it is desirable that the compositions be approximately isotonic with body fluids at the sites of injection. If the osmolality of a composition in the absence of a tonicity agent is sufficiently less than the osmolality of the tissue (for blood, about 300 mOsmol/kg; the European Pharmacopeial requirement for osmolality is >240 mOsmol/kg), then a tonicity agent should generally be added to raise the tonicity of the composition to about 300 mOsmol/kg. Typical tonicity agents are glycerol (glycerin) and sodium chloride. If the addition of a tonicity agent is required, glycerol is preferred. The amount of tonicity agent to add is readily determined using standard techniques. Remington: The Science and Practice of Pharmacy, David B. Troy and Paul Beringer, eds., Lippincott Williams & Wilkins, 2006, pp. 257-259; Remington: Essentials of Pharmaceutics, Linda Ed Felton, Pharmaceutical Press, 2013, pp. 277-300. In certain embodiments the concentration of glycerol is from about 1 to about 16 mg/mL.

In certain embodiments, the pharmaceutical composition is stable under storage and use conditions. When used herein, the term "stable" refers to both chemical and physical stability, as indicated, for example, by a loss of insulin potency of less than 5%, A-21 desamido formation of not more than 1.5%, development of substances other than insulin and A-21 desamido (collectively referred to as other related substances (ORS)) of not more than 4%, high molecular weight (HMW) formation of less than 1.5%, and the maintenance of a clear and colorless solution with no precipitate. Such properties may be measured by known techniques, including for example, those summarized in the studies described below. In certain embodiments, the pharmaceutical composition is stable to allow for storage of at least 24 months at 2-8° C. In certain embodiments, the pharmaceutical composition is stable to allow for up to 28 days in-use at temperatures of up to 30° C. for vials or cartridges in re-usable pen injectors. In certain embodiments, the pharmaceutical composition is stable to allow for storage of at least 36 months at 2-8° C. In certain embodiments, the pharmaceutical composition is stable to allow for up to 32 days in-use at temperatures of up to 30° C. for vials or cartridges in re-usable pen injectors. In certain embodiments, the composition is stable to allow for use in a pump device for continuous subcutaneous insulin infusion therapy for up to 7 days.

Citrate, which as noted above is added to contribute to improvements in time action, is also known to also have buffering properties at certain pH levels, but if desired an additional buffering compound may be included. Examples of such buffering compounds are phosphate buffers, such as dibasic sodium phosphate, or sodium acetate and tris(hydroxymethyl)aminomethane (TRIS). Phosphate or TRIS buffers are preferred. The pH for commercial insulin compositions is usually in the range of 7.2 to 7.6, with 7.4±0.1 as a common target pH. The pH of compositions of the present invention is typically 7.0 to 7.8 and it is adjusted using physiologically appropriate acids and bases, typically hydrochloric acid 10% and sodium hydroxide 10%. Preferably, the pH is about 7.4.

The route of administration for the compositions of the present invention will typically be by self-administered subcutaneous injection, e.g., by use of a syringe or a pen device, or by continuous subcutaneous insulin infusion therapy with an insulin pump device, though intravenous, intradermal, or intraperitoneal routes may also be used. Preferably, the route of administration is by self-administered subcutaneous injection. The dose of active agent injected will be determined by the patient in consultation with the patient's physician.

Additional embodiments of the present invention include those described below:

A pharmaceutical composition comprising: an insulin; citrate; zinc; magnesium; chloride; a surfactant; and a preservative.

The pharmaceutical composition of any of the above-described embodiments, wherein the insulin is selected from the group consisting of human insulin, insulin lispro, insulin aspart or insulin glulisine.

The pharmaceutical composition of any of the above-described embodiments, wherein the insulin is insulin lispro.

The pharmaceutical composition of any of the above-described embodiments, wherein the insulin concentration is from about 100 to about 500 U/mL.

The pharmaceutical composition of any of the above-described embodiments, wherein the insulin concentration is from about 100 to about 300.

The pharmaceutical composition of any of the above-described embodiments, wherein the insulin concentration is from about 100 to about 200 U/mL.

The pharmaceutical composition of any of the above-described embodiments, wherein the insulin concentration is about 100 U/mL. The pharmaceutical composition of any of the above-described embodiments, wherein the insulin concentration is about 100 U/mL.

The pharmaceutical composition of any of the above-described embodiments, wherein the concentration of citrate is from about 10 to about 35 mM.

The pharmaceutical composition of any of the above-described embodiments, wherein the concentration of citrate is from about 10 to about 30 mM.

The pharmaceutical composition of any of the above-described embodiments, wherein the concentration of citrate is from about 15 to about 35 mM.

The pharmaceutical composition of any of the above-described embodiments, wherein the concentration of citrate is from about 15 to about 30 mM.

The pharmaceutical composition of any of the above-described embodiments, wherein the concentration of citrate is from about 15 to about 25 mM.

The pharmaceutical composition of any of the above-described embodiments, wherein the concentration of citrate is from about 15 to about 20 mM.

The pharmaceutical composition of any of the above-described embodiments, wherein the concentration of citrate is from about 20 to about 25 mM.

The pharmaceutical composition of any of the above-described embodiments, wherein the concentration of zinc is from about 0.2 to about 2 mM.

The pharmaceutical composition of any of the above-described embodiments, wherein the concentration of zinc is from about 0.3 to about 1 mM.

The pharmaceutical composition of any of the above-described embodiments, wherein the concentration of zinc is from about 0.4 to about 1 mM.

The pharmaceutical composition of any of the above-described embodiments, wherein the concentration of zinc is from about 0.6 to about 0.9 mM.

The pharmaceutical composition of any of the above-described embodiments, wherein the molar ratio of magnesium to citrate is from about 1:10 to about 1:2.

The pharmaceutical composition of any of the above-described embodiments, wherein the molar ratio of magnesium to citrate is from about 1:5 to about 1:3.

The pharmaceutical composition of any of the above-described embodiments, wherein the concentration of magnesium is from about 1 to about 15 mM.

The pharmaceutical composition of any of the above-described embodiments, wherein the concentration of magnesium is from about 1 to about 5 mM.

The pharmaceutical composition of any of the above-described embodiments, wherein the concentration of magnesium is from about 5 to about 10 mM.

The pharmaceutical composition of any of the above-described embodiments, wherein the concentration of magnesium is from about 10 to about 15 mM.

The pharmaceutical composition of any of the above-described embodiments, wherein the concentration of magnesium is from about 3 to about 8 mM.

The pharmaceutical composition of any of the above-described embodiments, wherein the magnesium concentration is provided through the inclusion of magnesium chloride.

The pharmaceutical composition of any of the above-described embodiments, wherein the total chloride concentration is from about 10 to about 60 mM.

The pharmaceutical composition of any of the above-described embodiments, wherein the total chloride concentration is from about 15 to about 35 mM.

The pharmaceutical composition of any of the above-described embodiments, wherein the total chloride concentration is from about 15 to about 30 mM.

The pharmaceutical composition of any of the above-described embodiments, wherein the total chloride concentration is from about 20 to about 25 mM.

The pharmaceutical composition of any of the above-described embodiments, wherein the composition comprises sodium chloride in a concentration ranging from about 1 to about 50 mM.

The pharmaceutical composition of any of the above-described embodiments, wherein the composition comprises sodium chloride in a concentration ranging from about 1 to about 25 mM.

The pharmaceutical composition of any of the above-described embodiments, wherein the composition comprises sodium chloride in a concentration ranging from about 1 to about 20 mM.

The pharmaceutical composition of any of the above-described embodiments, wherein the concentration of surfactant is from about 0.001 to about 0.2% w/v.

The pharmaceutical composition of any of the above-described embodiments, wherein the surfactant is poloxamer 188.

The pharmaceutical composition of any of the above-described embodiments, wherein the concentration of poloxamer 188 is from about 0.003 to about 0.2% w/v.

The pharmaceutical composition of any of the above-described embodiments, wherein the concentration of poloxamer 188 is from about 0.03 to about 0.12% w/v.

The pharmaceutical composition of any of the above-described embodiments, wherein concentration of poloxamer 188 is from about 0.06 to about 0.09% w/v.

The pharmaceutical composition of any of the above-described embodiments, wherein the preservative is selected from the group consisting of phenol and metacresol. The pharmaceutical composition of any of the above-described embodiments, wherein the preservative is metacresol.

The pharmaceutical composition of any of the above-described embodiments, wherein the metacresol concentration is from about 2.5 to about 3.8 mg/mL.

The pharmaceutical composition of any of the above-described embodiments, further comprising a tonicity agent.

The pharmaceutical composition of any of the above-described embodiments, comprising glycerol as a tonicity agent.

The pharmaceutical composition of any of the above-described embodiments, comprising glycerol as a tonicity agent in a concentration from about 1 to about 16 mg/mL.

The pharmaceutical composition of any of the above-described embodiments, further comprising an additional buffer.

The pharmaceutical composition of any of the above-described embodiments, wherein the pH of the composition is from about 7.0 to about 7.8.

The pharmaceutical composition of any of the above-described embodiments, wherein the composition provides for an uptake of insulin into the blood that is at least 20% more rapid than for compositions which contain the same insulin but which do not contain citrate.

The pharmaceutical composition of any of the above-described embodiments, wherein the composition provides for an onset of action that is at least 20% more rapid than for compositions which contain the same insulin but which do not contain citrate.

The pharmaceutical composition of any of the above-described embodiments, wherein the composition provides for an uptake of insulin into the blood that is at least 30% more rapid than for compositions which contain the same insulin but which do not contain citrate.

The pharmaceutical composition of any of the above-described embodiments, wherein the composition provides for an onset of action that is at least 30% more rapid than for compositions which contain the same insulin but which do not contain citrate.

The pharmaceutical composition of any of the above-described embodiments, wherein the composition is stable to allow for storage of at least 24 months at 2-8° C.

The pharmaceutical composition of any of the above-described embodiments, wherein the composition is stable to allow for up to 28 days in-use at temperatures of up to 30° C. for vials or cartridges in re-usable pen injectors.

The pharmaceutical composition of any of the above-described embodiments, wherein the composition is stable to allow for storage of at least 36 months at 2-8° C.

The pharmaceutical composition of any of the above-described embodiments, wherein the composition is stable to allow for up to 32 days in-use at temperatures of up to 30° C. for vials or cartridges in re-usable pen injectors.

The pharmaceutical composition of any of the above-described embodiments, wherein the composition is stable to allow for use in a pump device for continuous subcutaneous insulin infusion therapy for up to 7 days.

The pharmaceutical composition of any of the above-described embodiments, wherein the composition does not include any additional chelating agent.

The pharmaceutical composition of any of the above-described embodiments, wherein the composition does not include EDTA.

The pharmaceutical composition of any of the above-described embodiments, wherein the composition does not include EDTA, ethylene glycol tetraacetic acid (EGTA), alginic acid, alpha lipoic acid, dimercaptosuccinic acid (DMSA), or 1,2-diaminocyclohexanetetraacetic acid (CDTA).

The pharmaceutical composition of any of the above-described embodiments, wherein the composition does not include any vasodilatory agent.

The pharmaceutical composition of any of the above-described embodiments, wherein the composition does not include any nitroglycerin.

The pharmaceutical composition of any of the above-described embodiments, wherein the composition does not include adenosine, endothelium-derived hyperpolarizing factor, a phosphodiesterase type 5 (PDES) inhibitor, a potassium channel opener, prostacyclin, forskolin, nitroglycerin, a nitric oxide forming agent, amyl nitrite, or nitroprusside.

The pharmaceutical composition of any of the above-described embodiments, wherein the composition does not include any oligosaccharides.

A method of treating diabetes comprising administering to a human in need thereof an effective dose of the pharmaceutical composition of any of the above-described embodiments.

The pharmaceutical composition of any of the above-described embodiments for use in therapy.

The pharmaceutical composition of any of the above-described embodiments for use in the treatment of diabetes.

The pharmaceutical composition of any of the above-described embodiments for use in the manufacture of a medicament for the treatment of diabetes.

A multi-use vial comprising any one of the pharmaceutical compositions of any of the above-described embodiments.

An re-usable pen injector comprising any one of the pharmaceutical compositions of any of the above-described embodiments.

A pump device for continuous subcutaneous insulin infusion therapy comprising any one of the pharmaceutical compositions of any of the above-described embodiments.

The invention is further illustrated by the following examples, which are not to be construed as limiting.

EXAMPLES

Pharmacokinetic and Pharmacodynamic Studies

Insulin Lispro Formulated With 35 mM Citrate, 0.3 mM Zinc, 5 mM $MgCl_2$ and 23 mM NaCl Diabetic (Alloxan induced), castrated, male Yucatan miniature swine with previously fitted vascular access ports were used under the supervision of staff and veterinarians. The diabetic animals are housed individually and have access to fresh water at all times. They are fed two meals per day of a standard diet and receive appropriate maintenance basal and prandial insulin twice per day to manage their diabetic condition.

Test article (Composition A in the table below) was formulated and shipped to the test site and Humalog® insulin control was a commercial vial on site at test site:

TABLE 1

| Name | Formulation Composition |
|---|---|
| Composition A | 108 U/mL insulin lispro<br>35 mM citrate<br>5 mM $MgCl_2$<br>23 mM NaCl<br>0.3 mM zinc<br>3.15 mg/mL m-cresol<br>pH 7.4 |

TABLE 1-continued

| Name | Formulation Composition |
|---|---|
| Humalog ® | 100 U/mL KPB<br>1.88 mg/mL dibasic sodium phosphate<br>16 mg/mL glycerol<br>3.15 mg/mL meta-cresol<br>0.3 mM zinc<br>pH 7.4 |

The day prior to study, animals were fed half their daily ration and received 0.2 U/kg Humalog® Mix 75/25 Insulin at their morning maintenance administration. All study animals were food-fasted overnight and did not receive their evening insulin or meal prior to drug administration on study day.

On the morning of study, all animals were placed into slings for restraint and had their vascular access ports accessed (equipped for blood sampling) and checked for patency. The animals were randomly placed into treatment groups. This was a full crossover design with n=13. One animal did not participate in the Composition A treatment group yielding n=12 for that treatment group.

After two baseline blood samples were collected (−30 and −20 min), the animals were returned to their pens and were fed ~300 g. Twenty minutes after the presentation of the fully consumed meal, the animals were injected with test article subcutaneously in the flank (0 min) with a Terumo insulin syringe (0.3 or 0.5 ml with ½" needle). All study animals had access to clean, fresh water throughout the remaining blood collection period.

Serial blood samples (2.0 mL each) were collected from each animal at the following time points: −30, −20 (then immediately Fed), 0 (just before dose), 5, 10, 15, 30, 45, 60, 75, 90, 105, 120, 150, 180, 240, and 360 minutes following the SC dosing.

Blood samples (anticoagulant: none [serum]) were maintained at ambient temperature for at least 30 minutes but no more than 2 hours to allow for clotting. Serum was then separated by centrifugation and divided into two aliquots and stored frozen at approximately −70° C.

Serum glucose concentrations were determined using an automated AU480 Clinical Chemistry Analyzer (Beckman Coulter, Inc., Brea, California). Aliquot for PK was shipped to EMD Millipore Corp., St. Charles, MO on dry ice by a next day shipping service and included a detailed sample manifest.

Serum glucose data are represented in Table 2 below as Mean (mg/dL)+/−SEM unless otherwise specified.

TABLE 2

| | Humalog ® | | Composition A | |
|---|---|---|---|---|
| Time (min) | AVG | SEM | AVG | SEM |
| −30 | 308.5 | 13.2 | 294.6 | 10.0 |
| −20 | 311.8 | 13.3 | 296.0 | 10.3 |
| 0 | 321.8 | 13.3 | 311.4 | 11.7 |
| 5 | 325.8 | 14.5 | 319.6 | 9.6 |
| 10 | 320.2 | 13.0 | 282.3 | 11.2 |
| 15 | 297.5 | 21.7 | 243.8 | 11.6 |
| 30 | 249.1 | 13.3 | 168.3 | 14.5 |
| 45 | 191.9 | 19.1 | 125.7 | 15.2 |
| 60 | 148.2 | 17.9 | 95.8 | 14.2 |
| 75 | 113.5 | 15.4 | 75.8 | 13.3 |
| 90 | 89.8 | 14.2 | 61.2 | 12.0 |
| 105 | 68.7 | 11.1 | 53.7 | 11.0 |
| 120 | 53.5 | 9.4 | 44.8 | 10.5 |
| 150 | 46.5 | 8.0 | 44.9 | 10.2 |

TABLE 2-continued

| Time (min) | Humalog ® AVG | Humalog ® SEM | Composition A AVG | Composition A SEM |
|---|---|---|---|---|
| 180 | 44.8 | 9.6 | 43.1 | 10.5 |
| 240 | 74.5 | 17.1 | 62.8 | 11.2 |
| 360 | 109.7 | 27.0 | 103.9 | 21.8 |

To statistically compare the change of serum glucose under different formulations at different time points, derivative analysis was utilized. The change of blood glucose at each time point is characterized by the first order derivative (instant directional change) at current time point. Polynomials of up to order 10 is fitted to the time course data for each individual animal. The optimal order of the polynomial is selected using Bayesian information Criterion (BIC). The rate of change at each time point is calculated as the derivative of the fitted polynomial curve at that time point. Once the derivatives are obtained, ANOVA model is fitted to compare the different formulations at each time. Animal to animal variation is accounted for in the ANOVA model. The contrasts are constructed to compare the different formulations and the p-values are adjusted using R package "multcomp." Animals are dosed after time 0; therefore, time 0 is not included in the analysis. For time points beyond 150 minutes, there are not enough time points to robustly estimate the derivative, therefore, these time points are also excluded in the statistical analysis.

Composition A resulted in a significantly ($p \leq 0.01$) faster decrease in serum glucose at 5, 10, and 15 minutes post dose compared to Humalog®.

Insulin levels for serum PK samples for the Composition A and Humalog® treatment groups are measured using a total insulin RIA. Lower and upper limits of quantitation for the assay are 20 pM and 5000 pM, respectively. Values below the lower limit of quantitation are assumed to be 20 pM. Non-compartmental pharmacokinetic analyses are performed using Phoenix WinNonlin v6.3.

TABLE 3

| Name | | Tmax (min) | Cmax (nM) | $AUC_{INF}$ (min*nM) | CL/F (mL/min/kg) |
|---|---|---|---|---|---|
| Humalog ® | Mean | 53.1 | 1.37 | 157 | 8.70 |
| N = 13 | SE | 7.52 | 0.246 | 16.9 | 0.871 |
| | Median | 45.0 | 1.04 | 127 | 9.48 |
| Composition A | Mean | 23.8 | 1.48 | 152 | 8.46 |
| N = 12 | SE | 6.07 | 0.130 | 10.5 | 0.822 |
| | Median | 12.5 | 1.35 | 154 | 7.80 |

Abbreviations:
Tmax—time to maximal concentration,
Cmax—maximum concentrations,
AUCINF—area under the curve from 0 to infinity,
CL/F—Clearance/bioavailability
Mean and median Tmax are 55% and 72% earlier in Composition A, respectively, than with Humalog.

Insulin Lispro Formulated with 25-35 mM Citrate, 0.285 mM Zinc, 5 mM MgCl2 and 15-23 mM NaCl.

A study of compositions comprising varying concentrations of citrate and zinc, magnesium chloride and sodium chloride is performed in diabetic (Alloxan induced), castrated, male Yucatan miniature swine following generally the procedures described above.

Test articles (Compositions A' and B in the table below) are formulated and shipped to the test site, and Humalog® insulin control is a commercial vial on site at test site:

TABLE 4

| Name | Formulation Composition |
|---|---|
| Composition A' | 95 U/mL insulin lispro |
| | 35 mM citrate |
| | 5 mM $MgCl_2$ |
| | 23 mM NaCl |
| | 0.285 mM zinc |
| | 2.99 mg/mL m-cresol |
| | 1.79 mg/mL dibasic sodium phosphate |
| | 15.2 mg/mL glycerol |
| | pH 7.4 |
| Composition B | 95 U/mL insulin lispro |
| | 25 mM citrate |
| | 5 mM $MgCl_2$ |
| | 15 mM NaCl |
| | 0.285 mM zinc |
| | 2.99 mg/mL m-cresol |
| | 1.79 mg/mL dibasic sodium phosphate |
| | 15.2 mg/mL glycerol |
| | pH 7.4 |
| Humalog ® | 100 U/mL KPB |
| | 1.88 mg/mL dibasic sodium phosphate |
| | 16 mg/mL glycerol |
| | 3.15 mg/mL meta-cresol |
| | 0.3 mM zinc |
| | pH 7.4 |

Study is designed as a 21 pig full cross-over design to study all pigs on all treatments (n=21). One animal is excluded from the Humalog® treatment group for baseline blood glucose <200 mg/dl, and one animal is excluded from the Humalog® treatment group for a non-patent port, so n=19 for that treatment group. One animal is excluded from the Composition A' treatment group for a reported miss dose at time of injection, so n=20 for that treatment group. One animal is excluded from the Composition B treatment group for baseline blood glucose <200 mg/dl, so n=20 for that treatment group.

Serum glucose data are presented in Table 5 below as mean (mg/dL)+/−SEM.

TABLE 5

| Time (min) | Humalog ® AVG | Humalog ® SEM | Composition A' AVG | Composition A' SEM | Composition B AVG | Composition B SEM |
|---|---|---|---|---|---|---|
| −30 | 291.1 | 8.9 | 288.3 | 8.7 | 284.1 | 11.4 |
| −20 | 296.8 | 8.7 | 296.5 | 9.3 | 289.0 | 12.6 |
| 0 | 311.5 | 10.6 | 311.1 | 10.5 | 297.5 | 13.8 |
| 5 | 320.3 | 8.9 | 319.9 | 10.6 | 296.8 | 15.2 |
| 10 | 319.5 | 9.8 | 299.2 | 12.6 | 280.4 | 14.4 |
| 15 | 306.3 | 11.8 | 265.0 | 14.3 | 248.7 | 16.5 |
| 30 | 262.8 | 17.1 | 206.8 | 21.9 | 185.5 | 19.3 |
| 45 | 223.6 | 19.4 | 177.1 | 24.3 | 156.0 | 20.8 |
| 60 | 195.7 | 19.6 | 162.4 | 24.4 | 140.9 | 20.9 |
| 75 | 168.3 | 19.2 | 148.3 | 23.6 | 131.0 | 21.9 |
| 90 | 150.3 | 18.4 | 139.8 | 22.9 | 112.9 | 19.1 |
| 105 | 130.0 | 17.0 | 128.5 | 21.5 | 107.5 | 18.1 |
| 120 | 122.8 | 17.2 | 123.2 | 20.9 | 95.4 | 16.5 |
| 150 | 89.6 | 12.7 | 107.7 | 19.6 | 76.5 | 13.2 |
| 180 | 70.1 | 10.6 | 98.3 | 18.0 | 66.0 | 11.3 |
| 240 | 64.2 | 9.9 | 92.8 | 16.3 | 66.0 | 9.8 |
| 360 | 79.0 | 12.4 | 100.3 | 15.2 | 90.3 | 11.0 |

To statistically compare the change of serum glucose under different formulations at different time points, derivative analysis, following generally the procedure described above, was utilized. Compositions A' and B each resulted in significantly ($p \leq 0.01$) faster decrease in serum glucose at 5, 10, and 15 minutes post dose compared to Humalog®.

Serum insulin concentrations and PK parameters are generated and analyzed generally as described above, and PK results are provided in table 6 below.

TABLE 6

| Compound | | Tmax (min) | Cmax (nM) | $AUC_{INF}$ (min*nM) | CL/F (mL/min/kg) |
|---|---|---|---|---|---|
| Humalog ® | Mean | 52.9 | 0.791 | 110 | 12.1 |
| N = 19 | SE | 6.42 | 0.137 | 10.1 | 0.906 |
| | Median | 45 | 0.569 | 97.9 | 12.3 |
| Composition A' | Mean | 48.8 | 0.757 | 106 | 12.6 |
| N = 20 | SE | 8.11 | 0.125 | 7.53 | 0.991 |
| | Median | 30 | 0.675 | 99.9 | 12.0 |
| Composition B | Mean | 27.3 | 0.885 | 101 | 13.3 |
| N = 20 | SE | 4.57 | 0.105 | 8.06 | 1.11 |
| | Median | 15 | 0.827 | 96.3 | 12.5 |

Median Tmax results are 33% and 67% earlier in Compositions A' and B than Humalog ®, and mean Tmax is 48% earlier in Composition B than Humalog.

Insulin Lispro Formulated with 15 mM Citrate, 0.285 mM Zinc, 5 mM MgCl2 and 15 mM NaCl A study on compositions comprising citrate, zinc, magnesium chloride and sodium chloride is performed in diabetic (Alloxan induced), castrated, male Yucatan miniature swine following generally the procedures described above. Composition C was formulated and shipped to the test site, and Humalog® control is a commercial vial.

TABLE 7

| Name | Formulation Composition |
|---|---|
| Composition C | 95 U/mL insulin lispro<br>15 mM citrate<br>5 mM $MgCl_2$<br>15 mM NaCl<br>0.285 mM zinc<br>2.99 mg/mL m-cresol<br>1.79 mg/mL dibasic sodium phosphate<br>15.2 mg/mL glycerol<br>pH 7.4 |
| Humalog ® | 100 U/mL KPB<br>1.88 mg/mL dibasic sodium phosphate<br>16 mg/mL glycerol<br>3.15 mg/mL meta-cresol<br>0.3 mM zinc<br>pH 7.4 |

Study is designed as a 13 pig full cross-over design to study all pigs on all treatments (n=13). One animal is excluded from the Composition C treatment group for baseline blood glucose <200 mg/dl, and one animal is excluded from the Composition C treatment group for a reported miss dose at time of injection, resulting in n=11 for that treatment group.

Serum glucose data are presented in Table 8 below as mean (mg/dL)+/−SEM.

TABLE 8

| | Humalog ® | | Composition C | |
|---|---|---|---|---|
| Time (min) | AVG | SEM | AVG | SEM |
| −30 | 292.2 | 9.4 | 297.8 | 10.6 |
| −20 | 302.6 | 9.1 | 306.9 | 11.0 |
| 0 | 316.8 | 12.0 | 324.4 | 10.7 |
| 5 | 319.9 | 12.3 | 330.8 | 12.8 |
| 10 | 312.9 | 13.2 | 312.0 | 11.2 |
| 15 | 311.4 | 14.8 | 288.4 | 15.1 |
| 30 | 248.7 | 22.2 | 225.5 | 15.0 |
| 45 | 203.5 | 22.9 | 189.1 | 18.7 |
| 60 | 162.8 | 23.9 | 152.2 | 19.9 |
| 75 | 135.6 | 24.7 | 125.0 | 20.6 |
| 90 | 116.2 | 25.4 | 98.1 | 17.8 |
| 105 | 99.5 | 23.4 | 84.2 | 17.7 |
| 120 | 85.6 | 22.5 | 69.8 | 15.6 |

TABLE 8-continued

| | Humalog ® | | Composition C | |
|---|---|---|---|---|
| Time (min) | AVG | SEM | AVG | SEM |
| 150 | 67.2 | 18.0 | 57.2 | 11.4 |
| 180 | 57.7 | 17.3 | 54.1 | 12.2 |
| 240 | 60.4 | 14.2 | 72.1 | 21.4 |
| 360 | 76.7 | 10.6 | 114.7 | 30.8 |

Composition C produced a shift in the glucose profiles compared to the Humalog ® control profile.

Serum insulin concentrations and PK parameters are generated and analyzed generally as described above, and PK results are provided in table 9 below.

TABLE 9

| Compound | | Tmax (min) | Cmax (nM) | $AUC_{INF}$ (min*nM) | CL/F (mL/min/kg) |
|---|---|---|---|---|---|
| Humalog ® | Mean | 64.6 | 0.703 | 106 | 12.3 |
| N = 13 | SE | 9.21 | 0.0955 | 9.10 | 1.09 |
| | Median | 60.0 | 0.643 | 99.5 | 12.1 |
| Composition C | Mean | 46.4 | 0.691 | 107 | 13.6 |
| N = 11 | SE | 8.20 | 0.111 | 17.6 | 1.58 |
| | Median | 45.0 | 0.540 | 92.5 | 13.0 |

Mean and median Tmax are 28% and 25% earlier in Composition C, respectively, than with Humalog.

Insulin Lispro Formulated with 25 mM Citrate, 0.285 mM Zinc and 25 mM NaCl

A study on compositions comprising 25 mM citrate, zinc and sodium chloride is performed in diabetic (Alloxan induced), castrated, male Yucatan miniature swine following generally the procedures described above.

Test article (Composition D in the table below) is formulated and shipped to the test site, and Humalog® insulin control was a commercial vial on site at test site:

TABLE 10

| Name | Formulation Composition |
|---|---|
| Composition D | 96 U/mL insulin lispro<br>25 mM citrate<br>25 mM NaCl<br>0.285 mM zinc<br>2.99 mg/mL m-cresol<br>1.79 mg/mL dibasic sodium phosphate<br>15.2 mg/mL glycerol<br>pH 7.4 |
| Humalog ® | 100 U/mL KPB<br>1.88 mg/mL dibasic sodium phosphate<br>16 mg/mL glycerol<br>3.15 mg/mL meta-cresol<br>0.3 mM zinc<br>pH 7.4 |

This study consists of three doses (0.1, 0.2, and 0.4 Units/Kg) of Composition D compared to Humalog® at the same doses. Study is designed as a 21 pig full cross-over design to study all pigs on all treatments (n=21). For 0.4 Unit/kg dose, two animals were excluded (one for illness and one for port non-patency) from the Composition D treatment group yielding n=19 for that treatment group. One animal was excluded from Humalog® 0.4 U/Kg treatment group (for port non-patency) yielding n=20 for that treatment group. All other doses n=21 for each treatment.

Serum glucose data are presented in Table 11 as mean (mg/dL)+/−SEM.

TABLE 11

| Time | Humalog ® 0.1 U/KG | | Composition D 0.1 U/KG | | Humalog ® 0.2 U/Kg | | Composition D 0.2 U/Kg | | Humalog ® 0.4 U/Kg | | Composition D 0.4 U/Kg | |
|---|---|---|---|---|---|---|---|---|---|---|---|---|
| (min) | AVG | SEM | AVG | SEM | AVG | SEM | AVG | SEM | AVG | SEM | AVG | SEM |
| −30 | 306.2 | 7.7 | 310.3 | 9.3 | 301.0 | 7.2 | 302.3 | 7.6 | 319.8 | 10.0 | 316.3 | 11.4 |
| −20 | 307.7 | 9.2 | 312.6 | 8.9 | 305.6 | 6.8 | 311.1 | 8.3 | 315.7 | 9.2 | 313.4 | 10.2 |
| 0 | 329.9 | 8.7 | 329.0 | 8.8 | 326.9 | 9.3 | 329.4 | 9.3 | 344.5 | 10.2 | 341.1 | 11.5 |
| 5 | 333.5 | 10.0 | 340.8 | 9.2 | 327.2 | 9.7 | 330.0 | 8.3 | 349.1 | 10.0 | 343.1 | 11.3 |
| 10 | 335.0 | 12.5 | 330.1 | 8.8 | 332.3 | 9.9 | 311.8 | 8.6 | 349.3 | 10.5 | 307.9 | 11.9 |
| 15 | 337.2 | 11.6 | 307.3 | 9.9 | 323.2 | 10.5 | 285.7 | 9.2 | 335.4 | 13.4 | 260.6 | 12.5 |
| 30 | 317.6 | 15.9 | 284.4 | 13.2 | 282.2 | 13.2 | 236.0 | 11.0 | 277.3 | 15.1 | 182.2 | 13.6 |
| 45 | 321.0 | 19.6 | 293.3 | 15.8 | 263.3 | 15.7 | 228.8 | 14.3 | 233.1 | 17.6 | 141.3 | 14.3 |
| 60 | 318.2 | 22.0 | 291.9 | 16.9 | 231.8 | 17.7 | 219.9 | 17.6 | 184.5 | 17.1 | 114.4 | 14.1 |
| 75 | 303.5 | 22.8 | 294.7 | 18.1 | 207.7 | 19.5 | 208.3 | 18.2 | 152.4 | 19.1 | 96.9 | 13.7 |
| 90 | 297.7 | 23.3 | 289.8 | 18.8 | 188.8 | 18.0 | 198.0 | 19.1 | 121.0 | 17.0 | 84.6 | 13.0 |
| 105 | 290.5 | 22.9 | 283.9 | 19.3 | 167.0 | 17.1 | 193.7 | 19.1 | 96.2 | 16.5 | 71.1 | 12.3 |
| 120 | 283.4 | 22.3 | 282.3 | 20.0 | 149.3 | 16.6 | 164.8 | 18.1 | 80.1 | 17.2 | 61.1 | 10.5 |
| 150 | 273.5 | 21.7 | 271.4 | 19.9 | 124.6 | 15.6 | 152.6 | 17.6 | 61.3 | 17.2 | 49.8 | 10.5 |
| 180 | 274.7 | 17.9 | 270.7 | 20.4 | 113.1 | 14.4 | 142.4 | 16.3 | 50.6 | 15.3 | 43.5 | 10.9 |
| 240 | 285.4 | 16.2 | 270.2 | 17.1 | 124.1 | 15.5 | 147.5 | 17.1 | 49.1 | 14.9 | 45.4 | 10.5 |
| 360 | 302.0 | 15.8 | 287.1 | 17.2 | 166.9 | 20.7 | 176.6 | 16.2 | 74.5 | 21.8 | 67.4 | 12.5 |

To statistically compare the change of serum glucose under different formulations at different time points, derivative analysis, following generally the procedure described above, was utilized. All three doses of Composition D (0.1, 0.2, and 0.4 U/kg) result in a significantly ($p \leq 0.01$) faster decrease of blood glucose level at time points 5, 10 and 15 minutes when compared against Humalog® at the same respective dose.

For pharmacokinetic analysis, eleven pigs were chosen at random using an online randomizing tool. Insulin levels for serum PK samples for those pigs are measured using a total insulin RIA. Lower and upper limits of quantitation for the assay are 20 pM and 5000 pM, respectively. Values below the lower limit of quantitation are assumed to be 20 pM. Non-compartmental pharmacokinetic analyses are performed using Phoenix WinNonlin v6.3.

TABLE 12

| Compound | | Tmax (min) | Cmax (nM) | $AUC_{INF}$ (min*nM) | CL/F (mL/min/kg) |
|---|---|---|---|---|---|
| 0.1 U/kg | Mean | 41.8 | 0.350 | 44.3 | 15.3 |
| Humalog ® | SE | 5.53 | 0.0531 | 5.20 | 1.62 |
| | Median | 45 | 0.283 | 43.5 | 13.8 |
| 0.1 U/Kg | Mean | 33.6 | 0.330 | 45.3 | 15.0 |
| Composition D | SE | 15.3 | 0.0546 | 5.70 | 1.60 |
| | Median | 15 | 0.231 | 38.3 | 15.7 |
| 0.2 U/Kg | Mean | 57.3 | 0.820 | 111 | 12.0 |
| Humalog ® | SE | 7.79 | 0.195 | 12.9 | 1.09 |
| | Median | 60 | 0.634 | 106 | 11.4 |
| 0.2 U/Kg | Mean | 53.6 | 1.14 | 132 | 10.7 |
| Composition D | SE | 14.6 | 0.258 | 17.5 | 1.41 |
| | Median | 30 | 0.847 | 115 | 10.5 |
| 0.4 U/Kg | Mean | 75 | 1.57 | 197 | 13.4 |
| Humalog ® | SE | 11.1 | 0.435 | 21.3 | 1.17 |
| | Median | 75 | 0.952 | 159 | 15.0 |
| 0.4 U/Kg | Mean | 48.6 | 3.19 | 327 | 8.58 |
| Composition D | SE | 13.2 | 0.975 | 46.6 | 0.961 |
| | Median | 45 | 2.16 | 304 | 7.89 |

Median Tmax values are 67%, 50% and 40% earlier in the 0.1 U/Kg, 0.2 U/Kg and 0.4 U/Kg Composition D groups as compared to those same doses with Humalog®. Mean Tmax values were 20% and 35% earlier in the 0.1 U/Kg and 0.4 U/Kg Composition D groups as compared to those same doses with Humalog®. Total exposure and Cmax appear greater for Composition D than Humalog® at the 0.2 U/kg and 0.4 U/kg doses.

Human Insulin, Insulin Aspart and Insulin Glulisine Formulated With 25 mM Citrate, and 5 mM $MgCl_2$ A study on compositions comprising three different insulins, 25 mM citrate and magnesium chloride is performed in diabetic (Alloxan induced), castrated, male Yucatan miniature swine following generally the procedures described above.

Test articles (Compositions E, F and G in the table below) are formulated by adding sufficient citrate and magnesium chloride to commercial vials of HUMULIN-R®, NOVOLOG® and APIDRA® to reach a concentration of 25 mM citrate and 5 mM magnesium chloride:

TABLE 13

| Name | Formulation Composition |
|---|---|
| Novolog ® | 100 U/mL insulin aspart<br>0.58 mg/mL NaCl<br>16 mg/mL glycerol<br>1.5 mg/mL phenol<br>1.72 mg/mL m-cresol<br>19.6 μ/mL Zn<br>pH 7.2-7.6 |
| Composition E | 97 U/mL insulin aspart<br>25 mM citrate<br>5 mM MgCl2<br>0.56 mg/mL NaCl<br>15.5 mg/mL glycerol<br>1.46 mg/mL phenol<br>1.67 mg/mL m-cresol<br>19.0 μ/mL Zn<br>pH 7.2-7.6 |
| Humulin-R ® | 100 U/mL human insulin<br>16 mg/mL glycerol<br>2.5 mg/mL m-cresol<br>0.015 mg/mL Zn<br>pH 7.0-7.8 |
| Composition F | 97 U/mL human insulin<br>25 mM citrate<br>5 mM MgCl2<br>15.5 mg/mL glycerol<br>2.43 mg/mL m-cresol<br>0.015 mg/mL Zn<br>pH 7.0-7.8 |
| Apidra ® | 100 U/mL insulin glulisine<br>3.15 mg/mL metacresol<br>6 mg/mL tromethamine<br>5 mg/mL NaCl<br>0.01 mg/mL polysorbate 20<br>pH 7.3 |

TABLE 13-continued

| Name | Formulation Composition |
|---|---|
| Composition G | 97 U/mL insulin glulisine |
| | 25 mM citrate |
| | 5 mM MgCl2 |
| | 3.06 mg/mL metacresol |
| | 5.8 mg/mL tromethamine |
| | 4.85 mg/mL NaCl |
| | 0.01 mg/mL polysorbate 20 |
| | pH 7.3 |

Study is designed as a full cross-over design to study all pigs on all treatments (n=20). One animal is excluded from Composition F treatment group for baseline blood glucose <200 mg/dl, resulting in n=19 for that group. Serum glucose data are presented in Table 14 as mean (mg/dL)+/−SEM.

TABLE 14

| Time | Novolog ® | | Composition E | | Humulin-R ® | | Composition F | | Apidra ® | | Composition G | |
|---|---|---|---|---|---|---|---|---|---|---|---|---|
| (min) | AVG | SEM | AVG | SEM | AVG | SEM | AVG | SEM | AVG | SEM | AVG | SEM |
| −30 | 340.9 | 8.2 | 338.1 | 5.8 | 313.2 | 7.7 | 319.7 | 8.5 | 298.3 | 8.4 | 287.9 | 6.4 |
| −20 | 353.7 | 7.8 | 348.9 | 6.7 | 324.2 | 7.7 | 325.7 | 8.2 | 310.4 | 9.1 | 299.0 | 6.5 |
| 0 | 363.4 | 9.5 | 361.2 | 8.2 | 334.1 | 10.3 | 337.5 | 10.2 | 319.5 | 10.6 | 302.9 | 8.5 |
| 5 | 377.1 | 10.4 | 374.3 | 8.7 | 346.9 | 10.4 | 350.6 | 10.9 | 329.6 | 10.7 | 309.6 | 9.5 |
| 10 | 378.4 | 11.2 | 362.8 | 10.1 | 355.5 | 10.6 | 342.5 | 12.2 | 334.7 | 11.9 | 304.2 | 10.7 |
| 15 | 380.8 | 12.5 | 343.9 | 12.4 | 360.3 | 10.9 | 340.8 | 14.2 | 331.7 | 13.2 | 290.2 | 12.8 |
| 30 | 362.1 | 16.1 | 294.4 | 18.8 | 367.4 | 13.8 | 332.4 | 17.8 | 323.8 | 18.0 | 257.1 | 17.3 |
| 45 | 330.6 | 19.1 | 269.8 | 21.6 | 376.9 | 15.6 | 328.7 | 20.0 | 320.1 | 20.5 | 244.4 | 19.6 |
| 60 | 302.2 | 22.0 | 241.6 | 21.4 | 370.8 | 17.4 | 326.9 | 22.5 | 304.4 | 21.3 | 233.1 | 19.2 |
| 75 | 285.9 | 25.2 | 225.1 | 21.8 | 360.3 | 19.1 | 318.7 | 22.9 | 283.1 | 21.6 | 223.6 | 19.3 |
| 90 | 254.1 | 26.3 | 205.4 | 20.4 | 351.0 | 19.8 | 306.4 | 22.9 | 261.2 | 21.8 | 208.3 | 17.9 |
| 105 | 230.4 | 26.3 | 188.0 | 19.7 | 330.7 | 19.9 | 289.6 | 23.0 | 239.0 | 20.9 | 200.9 | 18.3 |
| 120 | 196.1 | 24.8 | 159.4 | 17.9 | 308.7 | 21.1 | 269.9 | 22.4 | 211.1 | 20.4 | 181.5 | 17.6 |
| 150 | 152.9 | 23.8 | 140.3 | 17.6 | 267.3 | 25.4 | 216.9 | 22.5 | 169.1 | 20.8 | 150.5 | 18.1 |
| 180 | 111.1 | 20.9 | 120.0 | 16.3 | 207.0 | 22.5 | 167.7 | 19.7 | 130.1 | 19.1 | 126.7 | 16.8 |
| 240 | 71.4 | 12.7 | 107.3 | 17.7 | 130.7 | 21.1 | 107.6 | 15.9 | 84.5 | 14.3 | 79.4 | 11.6 |
| 360 | 65.8 | 8.5 | 90.4 | 16.9 | 70.4 | 17.9 | 45.1 | 8.0 | 62.6 | 10.4 | 50.5 | 5.8 |

The citrate-containing formulations of insulin aspart and human insulin produce a shift in the glucose profiles as compared to Novolog® and Humulin-R® controls, respectively. The citrate-containing formulation of insulin glulisine produces a less pronounced shift during approximately the first 90 minutes after dosing, as compared to Apidra® control.

Insulin Lispro Formulated with Varying Concentrations of Citrate, $MgCl_2$, Zinc, Surfactant and NaCl A study on compositions comprising varying concentrations of citrate, magnesium chloride, zinc, surfactant and/or sodium chloride is performed in diabetic (Alloxan induced), castrated, male Yucatan miniature swine following generally the procedures described above.

Test compositions H and J in the table below are prepared from bulk insulin lispro active pharmaceutical ingredient (API), and test articles I and K in the table below are prepared by adding citrate and the indicated stabilizing agents to a vial of Humalog® drug product, and shipped to the test site, and Humalog® insulin control is a commercial vial on site at test site.

TABLE 15

| Name | Formulation Composition |
|---|---|
| Composition H | 97.7 U/mL insulin lispro |
| | 25 mM citrate |
| | 5 mM MgCl2 |
| | 0.9 mM zinc |
| | 0.09% polysorbate 88 |
| | 5 mg/mL glycerin |
| Composition I | 91.4 U/mL insulin lispro |
| | 25 mM citrate |
| | 5 mM MgCl2 |
| | 15 mM NaCl |
| | 0.3 mM Zinc |
| | 14.6 mg/mL glycerin |
| Composition J | 97.6 U/mL insulin lispro |
| | 15 mM citrate |
| | 5 mM MgCl2 |
| | 15 mM NaCl |
| | 0.3 mM zinc |
| | 7.6 mg/mL glycerin |
| Composition K | 94 U/mL |
| | 25 mM citrate |
| | 5 mM MgCl2 |
| | 0.51 mM zinc |
| | 0.07% w/v P88 |
| | 15.2 mg/mL glycerin |
| Humalog ® | 100 U/mL KPB |
| | 1.88 mg/mL dibasic sodium phosphate |
| | 16 mg/mL glycerol |
| | 3.15 mg/mL meta-cresol |
| | 0.3 mM zinc |
| | pH 7.4 |

Study is designed as a full cross-over design to study all pigs on all treatments (n=19). One animal is excluded from each of the Composition I, J and K treatment groups for port failure or animal conditions resulting in n=18 for those treatment groups. Serum glucose data are presented in Table 16 as mean (mg/dL)+/−SEM.

TABLE 16

| Time | Humalog® | | Composition H | | Composition I | | Composition J | | Composition K | |
|---|---|---|---|---|---|---|---|---|---|---|
| (min) | AVG | SEM | AVG | SEM | AVG | SEM | AVG | SEM | AVG | SEM |
| −30 | 372.1 | 11.9 | 374.1 | 9.6 | 363.8 | 10.4 | 367.8 | 9.2 | 384.7 | 12.4 |
| −20 | 382.5 | 11.7 | 376.9 | 8.9 | 378.6 | 11.2 | 380.2 | 10.4 | 398.2 | 12.6 |
| 0 | 399.9 | 12.8 | 402.8 | 10.6 | 399.2 | 11.0 | 398.3 | 10.0 | 409.6 | 11.7 |
| 5 | 409.7 | 12.1 | 412.6 | 10.2 | 410.8 | 11.0 | 408.3 | 10.3 | 423.8 | 11.2 |
| 10 | 412.1 | 13.6 | 395.8 | 11.3 | 387.2 | 10.5 | 392.4 | 10.8 | 406.0 | 11.5 |
| 15 | 410.2 | 13.4 | 369.3 | 14.1 | 352.2 | 12.0 | 361.8 | 14.6 | 376.8 | 13.5 |
| 30 | 377.2 | 18.1 | 339.2 | 16.1 | 295.2 | 18.4 | 317.4 | 20.8 | 324.4 | 16.9 |
| 45 | 353.8 | 21.7 | 321.0 | 18.5 | 280.1 | 24.4 | 299.8 | 24.3 | 306.3 | 21.7 |
| 60 | 331.6 | 25.2 | 307.1 | 23.2 | 271.3 | 25.5 | 289.2 | 26.8 | 289.2 | 22.3 |
| 75 | 298.4 | 27.9 | 288.5 | 24.5 | 258.3 | 25.1 | 272.0 | 28.2 | 275.4 | 22.2 |
| 90 | 279.7 | 28.9 | 275.9 | 25.9 | 245.2 | 23.6 | 258.1 | 28.4 | 265.7 | 22.1 |
| 105 | 256.1 | 28.5 | 258.6 | 26.2 | 235.4 | 23.6 | 248.3 | 27.0 | 251.1 | 20.4 |
| 120 | 242.3 | 28.2 | 252.1 | 27.9 | 227.2 | 22.8 | 240.7 | 26.4 | 242.5 | 21.0 |
| 150 | 221.7 | 26.5 | 228.5 | 27.5 | 216.9 | 21.4 | 227.8 | 23.9 | 221.9 | 20.4 |
| 180 | 207.3 | 25.4 | 224.1 | 27.3 | 204.6 | 21.3 | 221.1 | 20.6 | 215.8 | 21.8 |
| 240 | 214.7 | 24.1 | 211.5 | 27.4 | 191.9 | 21.7 | 204.6 | 18.4 | 209.4 | 20.3 |
| 360 | 185.2 | 28.7 | 160.4 | 24.9 | 162.9 | 19.9 | 153.2 | 19.9 | 151.7 | 22.3 |

The citrate-containing formulations produce a shift in the glucose profiles as compared to Humalog® controls.

Serum insulin concentrations and PK parameters for Humalog® and Compositions H, J and K are generated and analyzed generally as described above, and PK results are provided in table 17 below.

TABLE 17

| Formulation | | Tmax (min) | Early ½ Tmax (min) | Late ½ Tmax (min) | Tmax spread (min) | T50 (min) |
|---|---|---|---|---|---|---|
| Humalog ® | Mean | 57.2 | 20.1 | 161 | 141 | 105 |
| | SE | 5.2 | 2.8 | 19 | 20 | 8 |
| Composition H | Mean | 55.0 | 9.76 | 129 | 119 | 96.8 |
| | SE | 11.0 | 2.07 | 13 | 13 | 6.7 |
| Composition J | Mean | 28.8 | 9.40 | 141 | 131 | 97.7 |
| | SE | 5.4 | 3.58 | 18 | 19 | 6.1 |
| Composition K | Mean | 56.2 | 16.7 | 115 | 98.3 | 89.3 |
| | SE | 13.7 | 6.0 | 18 | 19 | 5.8 |

Results indicate Compositions H, J and K have faster PK onset than Humalog®.

Stability Studies

Insulin Lispro Formulated with Varying Concentrations of Citrate, Sodium Chloride and Magnesium Chloride An accelerated shelf-life stability study is performed to assess the stability of insulin lispro when co-formulated with various concentrations of citrate, sodium chloride, and, optionally, magnesium chloride. Stability samples having the compositions set forth in the table below are prepared either by formulating insulin lispro active pharmaceutical ingredient with the other excipients indicated in the table below (Compositions L, M and N) or by adding citrate and sodium chloride to a vial of Humalog® drug product (Composition O).

TABLE 18

| Name | Formulation Composition |
|---|---|
| Composition L | 100 U/mL insulin lispro<br>35 mM sodium citrate<br>5 mM $MgCl_2$<br>23 mM NaCl<br>0.3 mM zinc oxide<br>3.15 mg/mL m-cresol<br>pH 7.5 |
| Composition M | 100 U/mL insulin lispro<br>25 mM citrate<br>5 mM $MgCl_2$<br>15 mM NaCl<br>0.3 mM zinc<br>3.15 mg/mL m-cresol<br>4.49 mg/mL glycerol<br>pH 7.5 |
| Composition N | 100 U/mL insulin lispro<br>15 mM citrate<br>5 mM $MgCl_2$<br>15 mM NaCl<br>0.3 mM zinc<br>3.15 mg/mL m-cresol<br>7.62 mg/mL glycerol<br>pH 7.5 |
| Composition O | 95 U/mL insulin lispro<br>25 mM citrate<br>25 mM NaCl<br>0.3 mM zinc<br>1.88 mg/mL dibasic sodium phosphate<br>3.15 mg/mL m-cresol<br>16 mg/mL glycerol<br>pH 7.5 |
| Humalog ® | 100 U/mL KPB<br>1.88 mg/mL dibasic sodium phosphate<br>16 mg/mL glycerol<br>3.15 mg/mL meta-cresol<br>0.3 mM zinc<br>pH 7.4 |

The solutions are filtered using 0.22 micron PVDF membrane (Cat# SLGV013SL, Millex, Millipore) and distributed into glass vials (Cat# NC4015-1, National Scientific, Thermo Scientific Inc.) with screw-top caps (Cat# C4015-67A, National Scientific, Thermo Scientific Inc.), incubated at 2 to 8° C. and 30° C. respectively. Samples from the 30° C. incubation temperature were pulled for analysis at initial, 8, 16, 27, 36, 44, 54 and 66 day time points. Samples from the 5° C. incubation temperature are pulled for analysis at initial, 27, 36, 44, 54 and 66 day time points.

Size exclusion high-performance liquid chromatography (SEC-HPLC) analysis is performed to assess protein potency and quantify high molecular weight species in each composition at the stability time points using a UV detector at 276 nm. Each sample (10 μL) is separated at room temperature by using a Sepax Zenix-C SEC-80, 7.8×300 mm, 3 μm particles column (catalog # 233080-7830) at a flow rate of 1.0 mL/minute with isocratic elution of mobile phase (0.1% TFA, 50% ACN) over a run time of 25 minutes.

Insulin concentrations are calculated by comparing the insulin peak area to an insulin lispro standard area and adjusting for purity determined by reverse phase HPLC. Results, reported in IU/mL, are given below.

TABLE 19

| 30° C. incubation temperature | | | | | | | | |
|---|---|---|---|---|---|---|---|---|
| | Day 0 | Day 8 | Day 16 | Day 27 | Day 36 | Day 44 | Day 54 | Day 66 |
| Composition L | 102.26 | 100.86 | 101.14 | 102.33 | 99.43 | 100.71 | 101.23 | 98.57 |
| Composition M | 102.83 | 102.46 | 100.06 | 104.37 | 100.48 | 100.99 | 101.29 | 99.99 |
| Composition N | 102.95 | 102.34 | 101.09 | 104.75 | 101.52 | 101.93 | 100.18 | 99.98 |
| Composition O | 93.44 | 94.24 | 92.49 | 97.27 | 91.20 | 91.65 | 90.83 | 89.96 |
| Humalog ® | 99.82 | 100.43 | 97.66 | 103.13 | 97.71 | 96.73 | 98.38 | 97.19 |

TABLE 20

| 4° C. incubation temperature | | | | | | |
|---|---|---|---|---|---|---|
| | Day 0 | Day 27 | Day 36 | Day 44 | Day 54 | Day 66 |
| Composition L | 102.26 | 104.63 | 102.93 | 102.87 | 105.14 | 102.59 |
| Composition M | 102.83 | 105.93 | 103.45 | 103.63 | 103.04 | 99.56 |
| Composition N | 102.95 | 106.56 | 103.25 | 102.83 | 102.69 | 104.28 |
| Composition O | 93.44 | 94.78 | 92.50 | 91.40 | 93.88 | 95.87 |
| Humalog ® | 99.82 | 103.94 | 97.82 | 99.76 | 97.92 | 99.74 |

Insulin loss for citrate-containing and Humalog® control samples is less than 5% for all samples out to 66 days at 4° C. and 30° C.

Percentage of high molecule weight (% HMW) is calculated by integrating the total area % of all peaks eluting prior to the main peak. Results (% HMW) are given in the tables below.

TABLE 21

| 30° C. incubation temperature | | | | | | | | |
|---|---|---|---|---|---|---|---|---|
| | Day 0 | Day 8 | Day 16 | Day 27 | Day 36 | Day 44 | Day 54 | Day 66 |
| Composition L | 0.18 | 0.20 | 0.27 | 0.37 | 0.40 | 0.45 | 0.50 | 0.63 |
| Composition M | 0.19 | 0.21 | 0.25 | 0.32 | 0.35 | 0.39 | 0.45 | 0.58 |
| Composition N | 0.16 | 0.21 | 0.25 | 0.32 | 0.36 | 0.43 | 0.46 | 0.57 |
| Composition O | 0.29 | 0.35 | 0.44 | 0.53 | 0.62 | 0.65 | 0.77 | 0.87 |
| Humalog ® | 0.30 | 0.34 | 0.43 | 0.57 | 0.65 | 0.69 | 0.81 | 0.97 |

TABLE 22

| 4° C. incubation temperature | | | | | | |
|---|---|---|---|---|---|---|
| | Day 0 | Day 27 | Day 36 | Day 44 | Day 54 | Day 66 |
| Composition L | 0.18 | 0.19 | 0.20 | 0.15 | 0.18 | 0.20 |
| Composition M | 0.19 | 0.17 | 0.18 | 0.15 | 0.19 | 0.19 |
| Composition N | 0.16 | 0.18 | 0.16 | 0.19 | 0.16 | 0.17 |
| Composition O | 0.29 | 0.34 | 0.36 | 0.34 | 0.31 | 0.35 |
| Humalog ® | 0.30 | 0.34 | 0.35 | 0.34 | 0.32 | 0.35 |

HMW formation is less than 1% for all citrate-containing and Humalog® control samples out to 66 days at 4° C. and 30° C.

Reversed phase high-performance liquid chromatography (RP-HPLC) analysis is performed to assess protein purity in each composition at the stability time points using a UV detector at 214 nm. Each sample (5 µL) is separated at 40° C. by using a Waters BioSuite C18 PA-B, 3.5 µm, 2.1×150 mm HPLC column (Part #186002435), or comparable column, at a flow rate of 0.6 mL/minute with mobile phase A (50 mM sulfate, pH 2.3+20% acetonitrile (v/v)) and mobile phase B (50 mM sulfate, pH 2.3+50% acetonitrile (v/v)). Gradient of mobile phase B at 0, 3, 15, 21, 26, 27, 27.5 and 35.0 min is 21, 25, 25, 30, 80, 80, 21 and 21%, respectively. Percentage of sample outside of main peak and A-21 desamido is determined by subtracting the main peak percentage and the A-21 desamido percentage from 100 percent. Collectively, these peaks are considered other related substances (ORS). The results (% outside of main peak and A-21 and desamido) are given below.

TABLE 23

| 30° C. incubation temperature | | | | | | | | |
|---|---|---|---|---|---|---|---|---|
| | Day 0 | Day 8 | Day 16 | Day 27 | Day 36 | Day 44 | Day 54 | Day 66 |
| Comp. L | 0.52 | 0.71 | 0.96 | 1.20 | 1.69 | 1.65 | 2.03 | 2.25 |
| Comp. M | 0.57 | 0.83 | 1.00 | 1.20 | 1.70 | 1.63 | 2.02 | 2.18 |
| Comp. N | 0.50 | 0.87 | 1.12 | 1.28 | 1.82 | 1.72 | 2.01 | 2.25 |
| Comp. O | 0.78 | 1.18 | 1.49 | 1.63 | 1.89 | 2.14 | 2.53 | 2.78 |
| Humalog ® | 0.74 | 1.15 | 1.47 | 1.68 | 1.77 | 2.20 | 2.63 | 2.97 |

TABLE 24

| 4° C. incubation temperature | | | | | |
|---|---|---|---|---|---|
| | Day 0 | Day 27 | Day 44 | Day 54 | Day 66 |
| Composition L | 0.52 | 0.62 | 0.59 | 0.66 | 0.68 |
| Composition M | 0.57 | 0.67 | 0.60 | 0.63 | 0.73 |
| Composition N | 0.50 | 0.66 | 0.59 | 0.67 | 0.76 |
| Composition O | 0.78 | 1.08 | 0.89 | 0.99 | 0.94 |
| Humalog ® | 0.74 | 1.05 | 0.87 | 0.95 | 0.91 |

The ORS for all citrate-containing and Humalog® control samples is less than 1.5% at 4° C. for 66 days and less than 3.0% at 30° C. for 66 days.

Physical Stability of Insulin Lispro Formulated with 25 mM Citrate, 0.3 mM Zinc, 5 mM $MgCl_2$, 0.09% Poloxamer and Varying Chloride Concentrations A lispro concentrate stock formulation is prepared comprising 200 U/mL insulin lispro/mL, 32 mg glycerin/mL, 6.30 mg metacresol/mL, 0.6 mM zinc in water for bulk sterile operations. The formulation is pH adjusted with hydrochloric acid to dissolve the insulin lispro and then adjusted with sodium hydroxide to pH of 7.45.

Test formulations are then prepared by diluting the insulin lispro concentrate with sodium citrate buffer, magnesium chloride hexahydrate powder, poloxamer 188 solution, and granular sodium chloride and q.s. with water for bulk sterile operations to a composition of 25 mM citrate, 5 mM $MgCl_2$, 0.09% poloxamer 188, 100 units/mL lispro, 16 mg/mL glycerin, 3.15 mg/mL Metacresol, and 0.3 mM zinc with either 23.2 (Composition P) or 17.7 (Composition Q) mM total chloride.

Formulations are sterile filtered and then volumetrically transferred to 10 mL glass vials with a 7 mL fill, stoppered, and crimp sealed.

In a thirteen day accelerated stability study (30° C., shaken 75 at strokes per minute (spm)) vials undergo visual inspection on days 2, 4, 8 and 13. Vials containing a clear and colorless solution with no precipitate are considered scored as a "pass," while a vial containing particulates or a solution which is not clear and/or discolored is recorded as "fail." Data are provided below in Table 25.

TABLE 25

| Composition | Day 2 (n = 2) | Day 4 (n = 2) | Day 8 (n = 4) | Day 13 (n = 4) |
|---|---|---|---|---|
| Composition P | 100% Pass | 100% Pass | 100% Pass | 50% pass |
| Composition Q | 100% Pass | 100% Pass | 100% Pass | 0% pass |

Physical Stability of Insulin Lispro Formulated with 25 mM Citrate, 0.3 mM Zinc, 0.09% Poloxamer and 23 mM Total Chloride with and without Magnesium A lispro concentrate stock formulation is prepared comprising 200 U/mL insulin lispro, 32 mg glycerin/mL, 6.30 mg metacresol/mL, and 0.6 mM zinc in water for bulk sterile operations. The formulation is pH adjusted with hydrochloric acid to dissolve the insulin lispro and then adjusted with sodium hydroxide to pH of 7.45.

Test formulations are prepared by diluting the lispro concentrate with sodium citrate buffer, poloxamer 188 solution, granular sodium chloride, optionally, with magnesium chloride hexahydrate powder, and q.s. with water for bulk sterile operations to compositions of 25 mM citrate, 0.09% w/v poloxamer 188, 100 units/mL lispro, 16 mg/mL glycerin, 3.15 mg/mL Metacresol, 0.3 mM zinc, 23 mM total chloride and either 0 (Composition R) or 5 (Composition S) mM $MgCl_2$.

Test formulations are sterile filtered and then volumetrically transferred to 10 mL glass vials with a 7 mL fill, stoppered, and crimp sealed.

Vials are subjected to a thirteen day accelerated stability study with periodic visual inspection following generally the method described above. Data are provided below in Table 26.

TABLE 26

| Composition | Day 2 (n = 2) | Day 4 (n = 2) | Day 8 (n = 4 ) | Day 10 (n = 4) | Day 13 (n = 4) |
|---|---|---|---|---|---|
| S | 100% Pass | 100% Pass | 100% Pass | 100% pass | 50% pass |
| R | 100% Pass | 50% Pass | 0% Pass | N/A | N/A |

Results support that magnesium improved the stability of Composition S relative to Composition R.

Physical Stability of Insulin Lispro Formulated with 25 mM Citrate, 5 mM $MgCl_2$, 20 mM Chloride, 0.6 mM Zinc, 0.09% Poloxamer A 69 day accelerated shelf life study is conducted on a formulation comprising 100 U/mL insulin lispro, 5 mM $MgCl_2$, 20 mM chloride, 0.6 mM zinc, 0.09% w/v poloxamer 188, 5 mg/mL glycerin and 3.15 mg/mL m-cresol (Composition T). A bulk concentrate formulation is prepared by dissolving of glycerin, metacresol, lispro and zinc oxide in water for bulk sterile operations by addition of HCl to lower the pH. After adjustment of pH to 7.4-7.5 with NaOH, a solution of appropriate concentration of citrate and additional stabilizing agents to achieve the final target excipient concentration of Composition T is added. This solution is made up of sodium citrate buffer, zinc chloride, magnesium chloride hexahydrate, and poloxamer 188 in water for bulk sterile operations. After adjustment of pH to 7.4-7.5, if needed, sodium chloride solution is added to achieve target total chloride concentration. The formulation is then q.s. to volume with water for bulk sterile operations.

Formulations are sterile filtered and then volumetrically transferred to 10 mL glass vials with a 10.3 mL fill, stoppered, and crimp sealed. Vials are stored static and upright at 30° C. and visual inspected, following generally the method described above, at days 36 and 69. All vials inspected at each timepoint pass (n=3 for day 36 and n=5 for day 69). These results support that Composition T remains clear and colorless with no precipitate in an accelerated shelf life study.

Insulin Lispro Formulated with Varying Concentrations of Citrate, Magnesium, Chloride, Zinc, Surfactant, Glycerin and TRIS Physical stability of the following seven formulations is tested in a 32-day simulated patient in use study:

TABLE 27

| Composition | Citrate (mM) | $MgCl_2$, (mM) | Total Cl− (mM) | Zn, (mM) | P88 (% w/v) | Glycerin (mg/mL) | TRIS, (mM) | m-cresol (mg/mL) |
|---|---|---|---|---|---|---|---|---|
| U | 25 | 5 | 21 | 0.6 | 0.12 | 5 | 0 | 3.15 |
| V | 25 | 5 | 21 | 0.9 | 0.09 | 5 | 0 | 3.15 |
| W | 25 | 8.3 | 31 | 0.6 | 0.06 | 5 | 0 | 3.15 |
| X | 20 | 5 | 20 | 0.6 | 0.09 | 5 | 0 | 3.15 |
| Y | 20 | 5 | 20 | 0.6 | 0.12 | 5 | 0 | 3.15 |
| Z | 25 | 5 | >30 | 0.6 | 0.09 | 1.3 | 40 | 3.15 |
| AA | 25 | 8.3 | 28 | 0.6 | 0.09 | 4.1 | 10 | 3.15 |

Concentrate lispro stock solutions are prepared by dissolving appropriate quantities of glycerin, metacresol, lispro, zinc oxide and, optionally, TRIS in water for bulk sterile operations by addition of HCl to lower the pH. Compositions of the two concentrate solutions are as follows: (1) 200 U/mL lispro, 12 mM total chloride, 10 mg/mL glycerin, 6.3 mg/mL Metacresol, 0.6 mM total zinc; and (2) 200 U/mL lispro, 51 mM total chloride, 2.6 mg/mL glycerin, 6.3 mg/mL Metacresol, 0.6 mM total zinc, 80 mM TRIS. The solutions are then pH adjusted to 7.4-7.5 with NaOH or HCl and filled to volume with water for bulk sterile operations.

Test compositions are prepared by diluting the lispro stock solutions by sequential addition of sodium citrate buffer, zinc in HCl solution, sodium hydroxide to adjust pH, magnesium chloride hexahydrate solution, poloxamer 188 solution, and sodium chloride solution. Compositions are sterile filtered and then volumetrically q.s. to volume with water for bulk sterile operations. Compositions are volumetrically transferred to 10 mL glass vials with a 10.3 mL fill, stoppered, and crimp sealed.

Compositions are stored at 30° C. and subjected to simulated in-use dosing conditions 3 times a day, as described in the following steps: obtain an insulin syringe and withdraw 8 units of air; insert the needle into the vial while the vial is in the upright position; ensure the needle tip does not touch the insulin solution; inject the air into the vial; while keeping the needle in the vial, turn the vial and syringe upside down; withdraw 8 units of the composition; if there are air bubbles in the syringe slowly move the plunger to push the bubble(s) back into the vial; adjust the syringe plunger so the final dosage is 8 units; remove the syringe and place vials back into 30° C. incubator.

Visual inspections, following generally the method described above, are conducted on days 15, 20, 25, 28 and 32. Data are provided in Table 28.

TABLE 28

| Composition | 15 Days (n = 5) | 20 Days (n = 5) | 25 Days (n = 5) | 28 Days (n = 5) | 32 Days (n = 5) |
|---|---|---|---|---|---|
| U | 100% Pass | 100% Pass | 100% Pass | 80% Pass | 80% Pass |
| V | 100% Pass | 100% Pass | 100% Pass | 100% Pass | 100% Pass |

TABLE 28-continued

| Composition | 15 Days (n = 5) | 20 Days (n = 5) | 25 Days (n = 5) | 28 Days (n = 5) | 32 Days (n = 5) |
|---|---|---|---|---|---|
| W | 100% Pass | 100% Pass | 100% Pass | 100% Pass | 100% Pass |
| X | 100% Pass | 100% Pass | 100% Pass | 100% Pass | 100% Pass |

TABLE 28-continued

| Composition | 15 Days (n = 5) | 20 Days (n = 5) | 25 Days (n = 5) | 28 Days (n = 5) | 32 Days (n = 5) |
|---|---|---|---|---|---|
| Y | 100% Pass | 100% Pass | 100% Pass | 80% Pass | 67% Pass |
| Z | 100% Pass | 100% Pass | 60% Pass | 10% Pass | 0% Pass |
| AA | 100% Pass | 80% Pass | 60% Pass | 20% Pass | 0% Pass |

Collectively, the studies described above demonstrate that compositions of insulin with certain specific concentrations of citrate and other excipients such as zinc, magnesium, chloride and surfactant have earlier onset of action, as well as earlier glucose lowering effects, and in certain embodiments are chemically and physically stable.

Sequences

```
Human insulin A-chain
                                        (SEQ ID NO: 1)
Gly Ile Val Glu Gln Cys Cys Thr Ser Ile Cys Ser

Leu Tyr Gln Leu Glu Asn Tyr Cys Asn.

Human insulin B-chain
                                        (SEQ ID NO: 2)
Phe Val Asn Gln His Leu Cys Gly Ser His Leu Val

Glu Ala Leu Tyr Leu Val Cys Gly Glu Arg Gly Phe

Phe Tyr Thr Pro Lys Thr.

Insulin lispro B-chain
                                        (SEQ ID NO: 3)
Phe Val Asn Gln His Leu Cys Gly Ser His Leu Val

Glu Ala Leu Tyr Leu Val Cys Gly Glu Arg Gly Phe

Phe Tyr Thr Lys Pro Thr.

Insulin aspart B-chain
                                        (SEQ ID NO: 4)
Phe Val Asn Gln His Leu Cys Gly Ser His Leu Val

Glu Ala Leu Tyr Leu Val Cys Gly Glu Arg Gly Phe

Phe Tyr Thr Asp Lys Thr.
```

-continued

| Sequences |
|---|
| Insulin glulisine B-chain (SEQ ID NO: 5)<br>Phe Val Lys Gln His Leu Cys Gly Ser His Leu Val<br>Glu Ala Leu Tyr Leu Val Cys Gly Glu Arg Gly Phe<br>Phe Tyr Thr Pro Glu Thr. |

wherein the concentration of magnesium does not exceed the concentration of citrate.

2. The pharmaceutical composition of claim 1, wherein the insulin is insulin lispro.

3. The pharmaceutical composition of claim 2, wherein the insulin lispro concentration is from about 100 to about 500 U/mL.

4. The pharmaceutical composition of claim 3, wherein the concentration of citrate is from about 15 to about 25 mM.

5. The pharmaceutical composition of any of claim 4, wherein the concentration of zinc is from about 0.3 to about 1.1 mM.

We claim:

1. A pharmaceutical composition comprising:

a. an insulin;

b. citrate, in a concentration from about 10 to about 30 mM;

c. zinc, in a concentration from about 0.2 to about 2 mM;

d. magnesium, in a concentration from about 1 to about 15 mM;

e. total chloride, in a concentration from about 10 to about 60 mM; and f. a preservative; and

6. The pharmaceutical composition of claim 1, wherein the magnesium concentration is provided through the inclusion of magnesium chloride.

7. The pharmaceutical composition of claim 6, wherein the magnesium concentration is from about 3 to about 8 mM.

8. The pharmaceutical composition of claim 1, wherein the total chloride concentration is from about 15 to about 35 mM.

9. The pharmaceutical composition of claim 8, wherein the total chloride concentration is from about 20 to about 25 mM.

10. The pharmaceutical composition of claim 1, comprising sodium chloride in a concentration ranging from about 1 to about 50 mM.

11. The pharmaceutical composition of claim 10, comprising sodium chloride in a concentration ranging from about 1 to about 25 mM.

12. The pharmaceutical composition of claim 11, comprising sodium chloride in a concentration ranging from about 1 to about 20 mM.

13. The pharmaceutical composition of claim 1, comprising a surfactant.

14. The pharmaceutical composition of claim 13, wherein the surfactant is poloxamer 188.

15. The pharmaceutical composition of claim 14, wherein the concentration of-poloxamer 188 is from about 0.003 to about 0.2% w/v.

16. The pharmaceutical composition of claim 1, wherein the preservative is selected from the group consisting of phenol and metacresol and mixtures thereof.

17. The pharmaceutical composition of claim 16, wherein the preservative is metacresol.

18. The pharmaceutical composition of claim 17, wherein the metacresol concentration is from about 2.5 to about 3.8 mg/mL.

19. The pharmaceutical composition of claim 1, wherein the molar ratio of magnesium to citrate is about 1:10 to about 1:2.

20. The pharmaceutical composition of claim 1, wherein the molar ratio of magnesium to citrate is about 1:5 to about 1:3.

21. The pharmaceutical composition of claim 1, wherein the composition does not include EDTA.

22. The pharmaceutical composition of claim 1, wherein the composition does not include any vasodilatory agent.

23. The pharmaceutical composition of claim 1, wherein the composition does not include any oligosaccharides.

24. The pharmaceutical composition of claim 1, wherein the chloride concentration does not crystalize insulin at low temperatures.

25. The pharmaceutical composition of claim 1, wherein the concentration of magnesium does not precipitate insulin.

26. A pharmaceutical composition comprising:

a. insulin lispro, in a concentration from about 100 to about 200 IU/mL;

b. citrate, in a concentration from about 15 to about 25 mM;

c. magnesium chloride, in a concentration to about 3 to about 8 mM;

d. zinc, in a concentration from about 0.6 to about 0.9 mM;

e. total chloride, in a concentration from about 20 to about 25 mM; and f. metacresol, in a concentration of about 2.8 to about 3.5 mg/mL; and wherein the pH of the composition is from about 7.0 to 7.8.

27. A pharmaceutical composition comprising:

a. insulin lispro, in a concentration of 100 IU/mL;

b. citrate, in a concentration of about 25 mM;

c. zinc, in a concentration from of about 0.9 mM;

d. magnesium chloride, in a concentration of about 5 mM;

e. total chloride, in a concentration from of about 20 to about 25 mM; and f. metacresol, in a concentration of about 3.15 mg/mL; and wherein the pH of the composition is about 7.4 mM.

28. A pharmaceutical composition comprising:

a. insulin lispro, in a concentration of 200 IU/mL;

b. citrate, in a concentration from about 15 to about 25 mM;

c. magnesium chloride, in a concentration of about 3 to about 8 mM;

d. zinc, in a concentration from about 0.6 to about 0.9 mM;

e. total chloride, in a concentration from about 20 to about 25 mM; and f. metacresol, in a concentration of about 2.8 to about 3.15 mg/mL; and wherein the pH of the composition is about 7.0 to 7.8.

29. A pharmaceutical composition comprising:

a. an insulin, in a concentration of about 100 to about 200 IU/mL;

b. citrate, in a concentration from about 15 to about 35 mM;

c. magnesium chloride, in a concentration of up to about 0.8 mM;

d. zinc, in a concentration from about 0.2 to about 0.8 mM;

e. sodium chloride, in a concentration from about 15 to about 25 mM;

f. a surfactant; and g. metacresol, in a concentration of about 2.8 to about 3.5 mg/mL; and wherein the pH of the composition is from about 7.0 to 7.8.

30. A method of treating diabetes comprising administering to a human in need thereof an effective dose of the pharmaceutical composition of claim 1.

* * * * *

SEQUENCE LISTING

```
Sequence total quantity: 5
SEQ ID NO: 1            moltype = AA  length = 21
FEATURE                 Location/Qualifiers
source                  1..21
                        mol_type = protein
                        organism = Homo sapiens
SEQUENCE: 1
GIVEQCCTSI CSLYQLENYC N                                       21

SEQ ID NO: 2            moltype = AA  length = 30
FEATURE                 Location/Qualifiers
source                  1..30
                        mol_type = protein
                        organism = Homo sapiens
SEQUENCE: 2
FVNQHLCGSH LVEALYLVCG ERGFFYTPKT                              30

SEQ ID NO: 3            moltype = AA  length = 30
FEATURE                 Location/Qualifiers
REGION                  1..30
                        note = Synthetic Construct
source                  1..30
                        mol_type = protein
                        organism = synthetic construct
SEQUENCE: 3
FVNQHLCGSH LVEALYLVCG ERGFFYTKPT                              30

SEQ ID NO: 4            moltype = AA  length = 30
FEATURE                 Location/Qualifiers
REGION                  1..30
                        note = Synthetic Construct
source                  1..30
                        mol_type = protein
                        organism = synthetic construct
SEQUENCE: 4
FVNQHLCGSH LVEALYLVCG ERGFFYTDKT                              30

SEQ ID NO: 5            moltype = AA  length = 30
FEATURE                 Location/Qualifiers
REGION                  1..30
                        note = Synthetic Construct
source                  1..30
                        mol_type = protein
                        organism = synthetic construct
SEQUENCE: 5
FVKQHLCGSH LVEALYLVCG ERGFFYTPET                              30
```